United States Patent [19]

Constansa et al.

[11] Patent Number: 4,933,338

[45] Date of Patent: Jun. 12, 1990

[54] BENZIMIDAZOLESULFONAMIDES AND THEIR APPLICATION AS DRUGS

[75] Inventors: Jordi F. Constansa; Juan P. Corominas; Agusto C. Piñol, all of Barcelone, Spain

[73] Assignee: Laboratorios del Dr. Esteve, S.A., Spain

[21] Appl. No.: 38,874

[22] Filed: Apr. 15, 1987

[30] Foreign Application Priority Data

Apr. 21, 1986 [FR] France .................. 86 05721

[51] Int. Cl.$^5$ ................ A61K 31/415; A61K 31/495; A61K 31/445; A61K 31/44; A61K 31/42; C07D 235/28; C07D 401/12; C07D 403/12

[52] U.S. Cl. .................. 514/234.5; 514/318; 514/322; 514/333; 514/338; 514/378; 514/395; 514/253; 514/232.5; 514/316; 544/80; 544/121; 544/129; 544/130; 544/131; 544/124; 544/137; 544/139; 544/357; 544/364; 544/367; 544/370; 544/360; 548/247; 548/329; 546/187; 546/193; 546/199; 546/256; 546/271

[58] Field of Search .............. 544/9, 133, 111, 80, 544/130, 137, 364, 360; 548/128; 546/271, 187, 256; 540/545, 470, 546

[56] References Cited

FOREIGN PATENT DOCUMENTS 687760 2/1950 United Kingdom .
833049 4/1960 United Kingdom .

OTHER PUBLICATIONS

Deshpande et al., Chemical Abstracts, vol. 85, entry 78049x (1976).
Knobloch et al., Chemical Abstracts, vol. 53, entry 3197(d-f), 1959.
Tamm et al., Chemical Abstracts, vol. 55, entry 16657 (d-f), 1961.
Stanovnik et al., Chemical Abstracts, vol. 63, entry 8342f (1965).
Nagel, Chemical Abstracts, vol. 91, entry 20983(e), 1979.
Heistand et al., Chemical Abstracts, vol. 88, entry 137866y (1978).
Stanovnik et al., Chemical Abstracts, vol. 67, entry 82161y (1967).

*Primary Examiner*—John M. Ford
*Attorney, Agent, or Firm*—Dressler, Goldsmith, Shore, Sutker & Milnamow, Ltd.

[57] ABSTRACT

Benzimidazole-2-sulfonamide and imidazopyridine-2-sulfonamide derivatives corresponding to the general formula I:

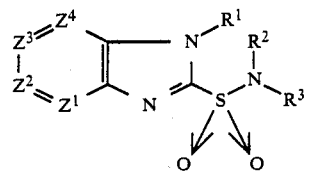

and their pharmaceutically acceptable salts, especially those of the formula in which:

$Z^1$ to $Z^4$ represent a nitrogen atom or a substituted or unsubstituted carbon atom;

$R^1$ and $R^2$ represent a hydrogen atom or an alkyl, alkylaryl, alkylcarbonylalkyl, alkylcarbonylaryl, alkylcarbonylheteroaryl, cycloalkyl, carboxyalkyl, acyl or nitro radical, or alternatively $R^1$ and $R^2$ can together form a linkage represented by a group X;

$R^3$ represents a hydrogen atom or an alkyl, aryl, heteroaryl, alkylaryl, hydroxyalkyl, alkylheteroaryl, mono-, bi- or tri-cycloalkyl, alkylamino, N-alkylalkylamino, alkylcarboxyalkyl, acyl, alkylthioalkyl, alkylsulfinylalkyl or alkylsulfonylalkyl, alkylthioaryl, alkylsulfinylaryl or alkylsulfonylaryl, alkylthioheteroaryl, alkylsulfinylheteroaryl or alkylsulfonylheteroaryl, alkylthioalkylaryl, alkylsulfinylalkylaryl or alkylsulfonylalkylaryl, alkylthioalkylheteroaryl, alkylsulfinylalkylheteroaryl or alkylsulfonylalkylheteroaryl, halogenoalkyl, cyanoalkyl, N-alkylarylalkylamino, N-alkyl-N-alkylaryl-alkylamino, N,N-dialkyl-alkylamino, alkylpiperazinyl, alkylpiperidinyl or alkylmorpholinyl radical;

X represents $-(CHR^8)_n-(CHR^9)_m-$ or $-CR^8=CR^9-$;

$R^8$ and $R^9$ represent a hydrogen atom or a lower alkyl, aryl or heteroaryl radical;

$R^{10}$ represents a hydrogen atom, a radical $-CH_2OH$, a radical $-CH_2Cl$ or a methylene radical $(-CH_2-)$;

$R^1$ can form a linkage with $R^{10}$ in the case where $R^{10}$ represents a methylene radical $(-CH_2-)$ and $R^1$ itself represents a linkage; and $R^{11}$ represents a hydrogen atom, an alkyl radical or a hydroxyalkyl radical.

5 Claims, No Drawings

BENZIMIDAZOLESULFONAMIDES AND THEIR APPLICATION AS DRUGS

The present invention relates to novel benzimidazole-2-sulfonamide and imidazopyridine-2-sulfonamide derivatives, the process for their preparation and their application as drugs.

The compounds forming the subject of the present invention can also be used in the pharmaceutical industry as intermediates and for the preparation of drugs.

Sulfonamides bonded to the 2-position of benzimidazole or imidazopyridines have been studied very little. To our knowledge, there are only a small number of publications in the scientific literature which refer to this kind of compound. Two publications in the sixties [B. Stanovuik and M. Tisler, *Arch. Pharm.*, 1965, 298, 357; B. Stanovuik and M. Tisler, *Arch. Pharm.* (Weinhem), 1967, 300, 322] describe the benzimidazole-2-sulfonamides N-substituted by the following radicals: m-chlorophenyl, phenyl, m-tolyl, morpholinyl, ethyl, propyl, n-octyl, n-decyl, n-hexadecyl, n-octadecyl and n-methylethoxymethylene. The second reference cited also describes the cyclization product 1,2,4-thiadiazolo[4,5-a]benzimidazole 1,1-dioxide. However, these papers neither describe nor suggest the use of these compounds for the therapeutic treatment of humans or animals.

Bis-benzimidazole-2-sulfonamides linked by aliphatic chains containing 2 to 12 carbon atoms have also been described as potential antidiabetics [S. M. Deshpande and K. C. Datta, *J. Indian Chem. Soc.*, 1976, 53, 320]. U.S. Pat. No. 2,603,649 (1952) and German Patent 27 26 625 (1977) claim only benzimidazole-2-sulfonamide and N,N-dimethylbenzimidazole-2-sulfonamide, respectively, without mentioning the use of these compounds for the therapeutic treatment of humans or animals. Finally, British Patents 687,760 and 833,049 also described benzimidazole-2-sulfonamide.

Our contribution has been to discover series of benzimidazole-2-sulfonamide and imidazopyridine-2-sulfonamide derivatives which possess pharmaceutical activities, in particular an ulcer-inhibiting activity and/or an antisecretory activity, and which are consequently useful as ulcer inhibitors or for treating gastric hypersecretion. In particular, the compounds are suitable for preventing or treating gastrointestinal diseases in mammals, including man, and mainly gastric acid secretion and cytoprotective capacity. The compounds are also useful as intermediates for the preparation of other compounds in these series.

The present invention relates to compounds of the general formula I:

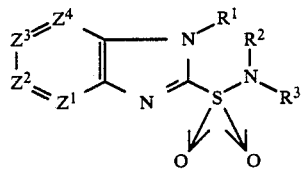

and their pharmaceutically acceptable salts, in which formula:

$Z^1$ represents a nitrogen atom or a carbon atom bonded to another radical $R^4$ (C—$R^4$);

$Z^2$ represents a nitrogen atom or a carbon atom bonded to another radical $R^5$ (C—$R^5$);

$Z^3$ represents a nitrogen atom or a carbon atom bonded to another radical $R^6$ (C—$R^6$);

$Z^4$ represents a nitrogen atom or a carbon atom bonded to another radical $R^7$ (C—$R^7$);

with the restriction that only one of the groups $Z^1$, $Z^2$, $Z^3$ or $Z^4$ can represent a nitrogen atom;

$R^1$ and $R^2$ independently represent a hydrogen atom, a linear or branched alkyl radical, an alkylaryl radical, an alkylcarbonylalkyl radical, an alkylcarbonylarylradical, an alkylcarbonylheteroaryl radical, a cycloalkyl radical, a carboxyalkyl radical, an acyl radical or a nitro radical, or alternatively $R^1$ and $R^2$ can together form a linkage represented by a group X;

$R^3$ represents a hydrogen atom, a linear or branched alkyl radical, an aryl radical, a heteroaryl radical, an alkylaryl radical, a hydroxyalkyl radical, an alkylheteroaryl radical, a mono-, bi- or tri-cycloalkyl radical, an alkylamino radical, an N-alkyl-alkylamino radical, an alkylcarboxyalkyl radical, an acyl radical, an alkylthioalkyl, alkylsulfinylalkyl or alkylsulfonylalkyl radical, an alkylthioaryl, alkylsulfinylaryl or alkylsulfonylaryl radical, an alkylthioheteroaryl, alkylsulfinylheteroaryl or alkylsulfonylheteroaryl radical, an alkylthioalkylaryl, alkylsulfinylalkylaryl or alkylsulfonylalkylaryl radical, an alkylthioalkylheteroaryl, alkylsulfinylalkylheteroaryl or alkylsulfonylalkylheteroaryl radical, a halogenoalkyl radical, a cyanoalkyl radical, an N-alkylaryl-alkylamino radical, an N-alkyl-N-alkylaryl-alkylamino radical, an N,N-dialkyl-alkylamino radical, an alkylpiperazinyl radical, an alkylpiperidinyl radical or an alkylmorpholinyl radical;

X represents —(CHR$^8$)$_n$—(CHR$^9$)$_m$— or —CR$^8$=CR$^9$—;

$R^2$ and $R^3$ can together form a linkage represented by a group —(CH$_2$)$_n$—Y$_m$—CHR$^{10}$—;

Y represents —CH$_2$—O—CH$_2$— or —CH$_2$—NR$^{11}$—CH$_2$—;

n represents 1, 2, 3 or 4;

m represents 0 or 1;

$R^4$ and $R^7$ independently represent a hydrogen atom, a halogen atom, a nitro radical, an amino radical or an acylamino radical (such as acetylamino);

$R^5$ and $R^6$ independently represent a hydrogen atom, a halogen atom, an amino radical, a nitro radical, a lower alkyl radical, a trifluoromethyl radical, an alkoxy radical, an aryloxy radical, a mercapto radical, an alkylthio radical, an alkylsulfinyl radical, an alkylsulfonyl radical, an isothiocyanate radical, a sulfamoyl radical, an alkylcarbonyl radical, an arylcarbonyl radical, an acylamino radical (such as acetylamino), a cyano radical, a carboxyl radical, a carboxamido radical or a carboxyalkyl radical;

$R^8$ and $R^9$ independently represent a hydrogen atom, a lower alkyl radical, an aryl radical or a heteroaryl radical;

$R^{10}$ represents a hydrogen atom, a radical —CH$_2$OH, a radical —CH$_2$Cl or a methylene radical (—CH$_2$—);

$R^1$ can form a linkage with $R^{10}$ in the case where $R^{10}$ represents a methylene radical (—CH$_2$—) and $R^1$ itself represents a linkage;

$R^{11}$ represents a hydrogen atom, an alkyl radical or a hydroxyalkyl radical;

Aryl represents a phenyl group or a substituted phenyl group; and

Heteroaryl represents an aromatic heterocyclic group in which the heteroatom or heteroatoms of the ring is/are selected from the group comprising O and N, it being possible for the heterocyclic group to be substituted.

It must be noted that, in the case where $R^1$ represents a hydrogen atom, the general formula I can be drawn as an alternative tautomeric form of the general formula I', as indicated, and any references made to the general formula I must, where necessary, include the alternative tautomeric form I'.

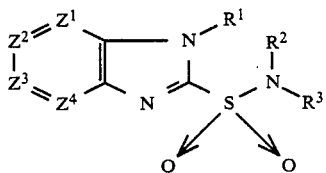

I'

The compounds of the general formula I and their physiologically acceptable salts are preferably administered in the form of pharmaceutical formulations.

A preferred group of compounds of the general formula I is that which corresponds to the compounds of the general formula Ia:

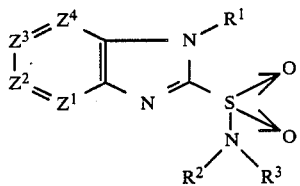

Ia in which:
$Z^1$ represents a nitrogen atom or a carbon atom bonded to another radical $R^4$ (C—$R^4$);
$Z^2$ represents a nitrogen atom or a carbon atom bonded to another radical $R^5$ (C—$R^5$);
$Z^3$ represents a nitrogen atom or a carbon atom bonded to another radical $R^6$ (C—$R^6$);
$Z^4$ represents a nitrogen atom or a carbon atom bonded to another radical $R^7$ (C—$R^7$);
with the restriction that only one of the groups $Z^1$, $Z^2$, $Z^3$ or $Z^4$ can represent a nitrogen atom;
$R^1$ represents a hydrogen atom, a linear or branched alkyl radical, an alkylaryl radical, an alkylcarbonylalkyl radical, an alkylcarbonylaryl radical, an alkylcarbonylheteroaryl radical, a cycloalkyl radical or a carboxyalkyl radical;
$R^2$ represents a hydrogen atom, a linear or branched $C_1$ to $C_5$ lower alkyl radical, a nitro radical or an acyl radical;
$R^3$ represents a hydrogen atom, a linear or branched alkyl radical, an aryl radical, a heteroaryl radical, an alkylaryl radical, an alkylheteroaryl radical, a mono-, bi- or tri-cycloalkyl radical, an alkylamino radical, an N-alkyl-alkylamino radical, an alkylcarboxyalkyl radical, an acyl radical, an alkylthioalkyl, alkylsulfinylalkyl or alkylsulfonylalkyl radical, an alkylthioaryl, alkylsulfinylaryl or alkylsulfonylaryl radical, an alkylthioheteroaryl, alkylsulfinylheteroaryl or alkylsulfonylheteroaryl radical, an alkylthioalkylaryl, alkylsulfinylalkylaryl or alkylsulfonylalkylaryl radical, an alkylthioalkylheteroaryl, alkylsulfinylalkylheteroaryl or alkylsulfonylalkylheteroaryl radical, a halogenoalkyl radical, a cyanoalkyl radical, an N-alkylaryl-alkylamino radical, an N-alkyl-N-alkylaryl-alkylamino radical, an N,N-dialkyl-alkylamino radical, a hydroxyalkyl radical, an alkylpiperazinyl radical, an alkylpiperidinyl radical or an alkylmorpholinyl radical;
$R^4$ and $R^7$ independently represent a hydrogen atom, a halogen atom, a nitro radical, an amino radical or an acylamino radical (such as acetylamino); and
$R^5$ and $R^6$ independently represent a hydrogen atom, a halogen atom, an amino radical, a nitro radical, a lower alkyl radical, a trifluoromethyl radical, an alkoxy radical, an aryloxy radical, a mercapto radical, an alkylthio radical, an alkylsulfinyl radical, an alkylsulfonyl radical, a sulfamoyl radical, an isothiocyanate radical, an alkylcarbonyl radical, an arylcarbonyl radical, an acylamino radical (such as acetylamino), a cyano radical, a carboxyl group, a carboxamidod group or a carboxyalkyl group.

A second preferred group of compounds of the general formula I is that which corresponds to the general formula Ib:

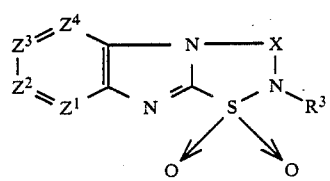

Ib in which:
$Z^1$ represents a nitrogen atom or a carbon atom bonded to another radical $R^4$ (C—$R^4$);
$Z^2$ represents a nitrogen atom or a carbon atom bonded to another radical $R^5$ (C—$R^5$);
$Z^3$ represents a nitrogen atom or a carbon atom bonded to another radical $R^6$ (C—$R^6$);
$Z^4$ represents a nitrogen atom or a carbon atom bonded to another radical $R^7$ (C—$R^7$);
with the restriction that only one of the groups $Z^1$, $Z^2$, $Z^3$ or $Z^4$ can represent a nitrogen atom;
$R^3$ represents a hydrogen atom, a linear or branched alkyl radical, an aryl radical, a heteroaryl radical, an alkylaryl radical, an alkylheteroaryl radical, a mono-, bi- or tri-cycloalkyl radical, an alkylamino radical, an N,N-dialkyl-alkylamino radical, an N-alkyl-alkylamino radical, an alkylcarboxyalkyl radical, an acyl radical, an alkylthioalkyl, alkylsulfinylalkyl or alkylsulfonylalkyl radical, an alkylthioaryl, alkylsulfinylaryl or alkylsulfonylaryl radical, an alkylthioheteroaryl, alkylsulfinylheteroaryl or alkylsulfonylheteroaryl radical, an alkylthioalkylaryl, alkylsulfinylalkylaryl or alkylsulfonylalkylaryl radical, an alkylthioalkylheteroaryl, alkylsulfinylalkylheteroaryl or alkylsulfonylalkylheteroaryl radical, a halogenoalkyl radical, a cyanoalkyl radical, an N-alkylaryl-alkylamino radica, an N-alkyl-N-alkylaryl-alkylamino radical, a hydroxyalkyl radical, an alkylpiperazinyl radical, an alkylpiperidinyl radical or an alkylmorpholinyl radical;
$R^4$ and $R^7$ independently represent a hydrogen atom, a halogen atom, a nitro radical, an amino radical or an acylamino radical (such as acetylamino);
$R^5$ and $R^6$ independently represent a hydrogen atom, a halogen atom, an amino radical, a nitro radical, a lower alkyl radical, a trifluoromethyl radical, an alkoxy radical, an aryloxy radical, a mercapto radical, an alkylthio radical, an alkylsulfinyl radical, an alkylsulfonyl radical, a sulfamoyl radical, an isothiocyanate radical, an alkylcarbonyl radical, an arylcarbonyl radical, an acylamino radical (such as acetylamino), a cyano radical, a carboxyl group, a carboxamido group or a carboxyalkyl group;

X represents —(CHR$^8$)$_n$—(CHR$^9$)$_m$— or —CR$^8$=CR$^9$—;

n represents 1, 2, 3 or 4;

m represents 0 or 1; and

R$^8$ and R$^9$ independently represent a hydrogen atom, a lower alkyl radical, an aryl radical or a heteroaryl radical.

A third preferred group of compounds of the general formula I is that which corresponds to the compounds of the general formula Ic:

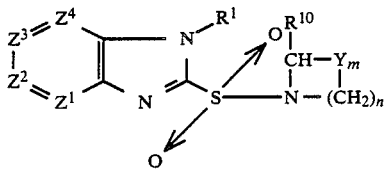

Ic in which:

Z$^1$ represents a nitro atom or a carbon atom bonded to another radical R$^4$ (C—R$^4$);

Z$^2$ represents a nitrogen atom or a carbon atom bonded to another radical R$^5$ (C—R$^5$);

Z$^3$ represents a nitrogen atom or a carbon atom bonded to another radical R$^6$ (C—R$^6$);

Z$^4$ represents a nitrogen atom or a carbon atom bonded to another radical R$^7$ (C—R$^7$);

with the restriction that only one of the groups Z$^1$, Z$^2$, Z$^3$ or Z$^4$ can represent a nitrogen atom;

R$^1$ represents a hydrogen atom, a linear or branched alkyl radical, an alkylaryl radical or a carboxyalkyl radical;

Y represents —CH$_2$—O—CH$_2$— or —CH$_2$—NR$^{11}$—CH$_2$—;

n represents 1, 2, 3 or 4;

m represents 0 or 1;

R$^4$ and R$^7$ independently represent a hydrogen atom, a halogen atom, a nitro radical, an amino radical or an acylamino radical (such as acetylamino);

R$^5$ and R$^6$ independently represent a hydrogen atom, a halogen atom, an amino radical, a nitro radical, a lower alkyl radical, a trifluoromethyl radical, an alkoxy radical, an aryloxy radical, a mercapto radical, an alkylthio radical, an alkylsulfinyl radical, an alkylsulfonyl radical, a sulfamoyl radical, an isothiocyanate radical, an alkylcarbonyl radical, an arylcarbonyl radical, an acylamino radical (such as acetylamino), a cyano radical, a carboxyl group, a carboxamido group or a carboxyalkyl group;

R$^{10}$ represents a hydrogen atom, a hydroxyalkyl radical, a halogenoalkyl radical or a carboxyalkyl radical; and R$^{11}$ represents a hydrogen atom, a lower alkyl radical or a hydroxyalkyl radical.

A fourth preferred group of compounds of the general formula I is that which corresponds to the compounds of the general formula Id:

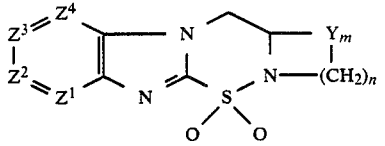

Id in which:

Z$^1$ represents a nitrogen atom or a carbon atom bonded to another radical R$^4$ (C—R$^4$);

Z$^2$ represents a nitrogen atom or a carbon atom bonded to another radical R$^5$ (C—R$^5$);

Z$^3$ represents a nitrogen atom or a carbon atom bonded to another radical R$^6$ (C—R$^6$);

Z$^4$ represents a nitrogen atom or a carbon atom bonded to another radical R$^7$ (C—R$^7$);

with the restriction that only one of the groups Z$^1$, Z$^2$, Z$^3$ or Z$^4$ can represent a nitrogen atom;

Y represents —CH$_2$—O—CH$_2$— or —CH$_2$—NR$^{11}$—CH$_2$—;

n represents 1, 2, 3 or 4;

m represents 0 or 1;

R$^4$ and R$^7$ independently represent a hydrogen atom, a halogen atom, a nitro radical, an amino radical or an acylamino radical (such as acetylamino);

R$^5$ and R$^6$ independently represent a hydrogen atom, a halogen atom, an amino radical, a nitro radical, a lower alkyl radical, a trifluoromethyl radical, an alkoxy radical, an aryloxy radical, a mercapto radical, an alkylthio radical, an alkylsulfinyl radical, an alkylsulfonyl radical, a sulfamoyl radical, an isothiocyanate radical, an alkylcarbonyl radical, an arylcarbonyl radical, an acylamino radical (such as acetylamino), a cyano radical, a carboxyl group, a carboxamido group or a carboxyalkyl group; and R$^{11}$ represents a hydrogen atom, a lower alkyl radical or a hydroxyalkyl radical.

The classes of particularly preferred compounds of the general formula I include the following compounds:

5-Benzoyl-N-ethyl-1H-benzimidazole-2-sulfonamide.
N-Methyl-1H-benzimidazole-2-sulfonamide.
N-(2-Pyridyl)-1H-benzimidazole-2-sulfonamide.
N-[2-(4-Morpholinoethyl)]-1H-benzimidazole-2-sulfonamide.
N-(4-Aminobutyl)-1H-benzimidazole-2-sulfonamide.
N-[3-(4-Morpholinopropyl)]-1H-benzimidazole-2-sulfonamide.
5-Chloro-N-ethyl-1H-benzimidazole-2-sulfonamide.
5-Phenoxy-N-ethyl-1H-benzimidazole-2-sulfonamide.
N-[2-(3,4-Dimethoxyphenylethyl)]-1H-benzimidazole-2-sulfonamide.
N,N-Diethyl-1H-benzimidazole-2-sulfonamide.
N-Butyl-1H-benzimidazole-2-sulfonamide.
N-Ethyl-4,7-dichloro-5,6-dimethyl-1H-benzimidazole-2-sulfonamide.
N-(4-Chlorophenyl)-1H-benzimidazole-2-sulfonamide.
5-Chloro-N-(4-chlorophenyl)-1H-benzimidazole-2-sulfonamide.
5-Chloro-N-(4-diethylamino-1-methylbutyl)-1H-benzimidazole-2-sulfonamide.
4-Chloro-5,6-dimethyl-N-ethyl-1H-benzimidazole-2-sulfonamide.
4-Nitro-1H-benzimidazole-2-sulfonamide.
N-Ethyl-4-nitro-1H-benzimidazole-2-sulfonamide.
N-(4-Diethylamino-1-methylbutyl)-1H-benzimidazole-2-sulfonamide.
N-Cyanomethyl-1H-benzimidazole-2-sulfonamide.
N-Cyclohexyl-1H-benzimidazole-2-sulfonamide.
N-(1-Naphthyl)-1H-benzimidazole-2-sulfonamide.
N-Ethyl-5-trifluoromethyl-1H-benzimidazole-2-sulfonamide.
N-(1-Adamantyl)-1H-benzimidazole-2-sulfonamide.
2-(Sulfonyl-2-hydroxymethyl-1-piperidinyl)-1H-benzimidazole.

N-(4-Methoxybenzyl)-1H-benzimidazole-2-sulfonamide.
N-(5-Methyl-3-isoxazolyl)-1H-benzimidazole-2-sulfonamide.
N-(2-Pyridylmethyl)-1H-benzimidazole-2-sulfonamide.
N-[2-(2-Pyridylethyl)]-1H-benzimidazole-2-sulfonamide.
5-Benzoyl-N-(4-diethylamino-1-methylbutyl)-1H-benzimidazole-2-sulfonamide.
5-Nitro-1H-benzimidazole-2-sulfonamide.
N-Ethyl-5-nitro-1H-benzimidazole-2-sulfonamide.
N-[2-(4-Morpholinoethyl)]-5-nitro-1H-benzimidazole-2-sulfonamide.
N,N-Diethyl-5-nitro-1H-benzimidazole-2-sulfonamide.
N-[3-(4-Morpholinopropyl)]-5-nitro-1H-benzimidazole-2-sulfonamide.
N-Butyl-4-nitro-1H-benzimidazole-2-sulfonamide.
N-(2-Hydroxy-1-ethyl)-4-nitro-1H-benzimidazole-2-sulfonamide.
N-Carboxyethylmethyl-4-nitro-1H-benzimidazole-2-sulfonamide.
N-Ethyl-N,4-dinitro-1H-benzimidazole-2-sulfonamide.
N-[2-(4-Morpholinoethyl)]-4-nitro-1H-benzimidazole-2-sulfonamide.
N-Acetyl-N-ethyl-4-nitro-1H-benzimidazole-2-sulfonamide.
N-Acetyl-4-nitro-1H-benzimidazole-2-sulfonamide.
2-[Sulfonyl-4-(2-hydroxy-1-ethyl)piperazinyl]-4-nitro-1H-benzimidazole.
N-(4-Fluorophenyl)-4-nitro-1H-benzimidazole-2-sulfonamide.
2-[Sulfonyl-2-(carboxymethyl)pyrrolidinyl]-4-nitro-1H-benzimidazole.
N-Methyl-4-nitro-1H-benzimidazole-2-sulfonamide.
N-Propyl-4-nitro-1H-benzimidazole-2-sulfonamide.
N-Isopropyl-4-nitro-1H-benzimidazole-2-sulfonamide.
N-Ethylthioethyl-4-nitro-1H-benzimidazole-2-sulfonamide.
N-Ethylsulfonylethyl-4-nitro-1H-benzimidazole-2-sulfonamide.
N-[3-(2-Oxohexamethyleneiminyl)]-4-nitro-1H-benzimidazole-2-sulfonamide.
N-[1-[1,3-Bis(carboxyethyl)propyl]]-4-nitro-1H-benzimidazole-2-sulfonamide.
2-[Sulfonyl-4-methylpiperazinyl]-1H-benzimidazole.
5-Chloro-N-cyclohexyl-1H-benzimidazole-2-sulfonamide.
N-(2-Diethylamino-1-ethyl)-1H-benzimidazole-2-sulfonamide.
N-Ethyl-1H-imidazo[4,5-b]pyridine-2-sulfonamide.
N-Butyl-1H-imidazo[4,5-b]pyridine-2-sulfonamide.
N-Butyl-1H-imidazo[4,5-c]pyridine-2-sulfonamide.
1,N-Diethyl-1H-benzimidazole-2-sulfonamide.
1,N,N-Triethyl-1H-benzimidazole-2-sulfonamide.
1,N-Dimethyl-N-ethyl-1H-benzimidazole-2-sulfonamide.
1-Benzoylmethyl-N-ethyl-1H-benzimidazole-2-sulfonamide.
1-Acetylmethyl-N-ethyl-1H-benzimidazole-2-sulfonamide.
N-Ethyl-1-(2-pyridylcarbonylmethyl)-1H-benzimidazole-2-sulfonamide.
5-Chloro-N-(4-diethylamino-1-methylbutyl)-1-ethyl-1H-benzimidazole-2-sulfonamide.
6-Chloro-N-(4-diethylamino-1-methylbutyl)-1-ethyl-1H-benzimidazole-2-sulfonamide.
1,N-Diethyl-4-nitro-1H-benzimidazole-2-sulfonamide.
1,N,N-Triethyl-6-nitro-1H-benzimidazole-2-sulfonamide.
1,N,N-Triethyl-5-nitro-1H-benzimidazole-2-sulfonamide.
5-Chloro-1,N-diethyl-N-(4-diethylamino-1-methylbutyl)-1H-benzimidazole-2-sulfonamide.
6-Chloro-1,N-diethyl-N-(4-diethylamino-1-methylbutyl)-1H-benzimidazole-2-sulfonamide.
1,N,N-Triethyl-4-nitro-1H-benzimidazole-2-sulfonamide.
1,N,N-Triethyl-7-nitro-1H-benzimidazole-2-sulfonamide.
1,N-Diethyl-5,N-dinitro-1H-benzimidazole-2-sulfonamide.
1,N-Diethyl-6,N-dinitro-1H-benzimidazole-2-sulfonamide.
1,N-Diethyl-5-nitro-1H-benzimidazole-2-sulfonamide.
1,N-Diethyl-6-nitro-1H-benzimidazole-2-sulfonamide.
5-Amino-1H-benzimidazole-2-sulfonamide.
4-Amino-1H-benzimidazole-2-sulfonamide.
4-Amino-N-(carboxyethylmethyl)-1H-benzimidazole-2-sulfonamide.
4-Amino-N-ethyl-1H-benzimidazole-2-sulfonamide.
4-Acetylamino-N-ethyl-1H-benzimidazole-2-sulfonamide.
3,4-Dihydro-2H-2-ethyl-[1,2,5]-thiadiazino[5,6-a]benzimidazole 1,1-dioxide.
3,4-Dihydro-2H-[1,2,5]-thiadiazino[5,6-a]benzimidazole 1,1-dioxide.
3,4-Dihydro-2H-2-methyl-[1,2,5]-thiadiazino[5,6-a]benzimidazole, 1,1-dioxide.
3,4,5-Trihydro-2H-2-methyl-[1,2,6]-thiadiazepino[6,7-a]benzimidazole 1,1-dioxide.
3,4,5-Trihydro-2H-2-ethyl-[1,2,6]-thiadiazepino[6,7-a]benzimidazole 1,1-dioxide.
3,4,5,6-Tetrahydro-2H-2-ethyl-[1,2,7]-thiadiazocino[7,8-a]benzimidazole 1,1-dioxide.
3,4-Dihydro-2H-[3-(4-morpholinopropyl)]-[1,2,5]thiadiazino[5,6-a]benzimidazole 1,1-dioxide.
3,4,5-Trihydro-2H-[2-(4-morpholinoethyl)]-[1,2,6]thiadiazepino[6,7-a[benzimidazole 1,1-dioxide.
3,4-Dihydro-2H-2-ethyl-8-phenoxy-[1,2,5]-thiadiazino[5,6-a]benzimidazole 1,1-dioxide.
3,4-Dihydro-2H-2-ethyl-7-phenoxy-[1,2,5]-thiadiazino[5,6-a]benzimidazole 1,1-dioxide.
8-Chloro-3,4-dihydro-2H-2-ethyl-7-phenoxy-[1,2,5]-thiadiazino[5,6-a]benzimidazole 1,1-dioxide.
7-Chloro-3,4-dihydro-2H-2-ethyl-7-phenoxy-[1,2,5]-thiadiazino[5,6-a]benzimidazole 1,1-dioxide.
3,4,5-Trihydro-2H-[1,2,6]-thiadiazepino[6,7-a]benzimidazole 1,1-dioxide.
3,4-Dihydro-2H-2-[2-(3,4-dimethoxyphenylethyl)]-[1,2,5]-thiadiazino[5,6-a]benzimidazole 1,1-dioxide.
2H-2-Butyl-3,4-Dihydro-[1,2,5]-thiadiazino[5,6-a]benzimidazole 1,1-dioxide.
6,9-Dichloro-3,4-dihydro-7,8-dimethyl-2H-2-ethyl-[1,2,5]-thiadiazino[5,6-a]benzimidazole 1,1-dioxide.
8-Chloro-3,4-dihydro-2H-2-(4-diethylamino-1-methylbutyl)-[1,2,5]-thiadiazino[5,6-a]benzimidazole 1,1-dioxide.
7-Chloro-3,4-dihydro-2H-2-(4-diethylamino-1-methylbutyl)-[1,2,5]-thiadiazino[5,6-a]benzimidazole 1,1-dioxide.
2H-2-(4-Chlorophenyl)-3,4-dihydro-[1,2,5]-thiadiazino[5,6-a]benzimidazole 1,1-dioxide.
3,4-Dihydro-2H-2-(5-methyl-3-isoxazolyl)-[1,2,5]-thiadiazino[5,6-a]benzimidazole 1,1-dioxide.

2H-2-(4-Diethylamino-1-methylbutyl)-3,4-dihydro[1,2,5]-thiadiazino[5,6-a]benzimidazole 1,1-dioxide.
3,4-Dihydro-2H-2-ethyl-9-nitro-[1,2,5]-thiadiazino[5,6-a]benzimidazole 1,1-dioxide.
3,4-Dihydro-2H-2-ethyl-6-nitro-[1,2,5]-thiadiazino[5,6-a]benzimidazole 1,1-dioxide.
3-Hydro-2H-2-methyl-6-nitro-[1,2,4]-thiadiazolo[4,5-a]benzimidazole 1,1-dioxide.
2H-2-Cyclohexyl-3,4-dihydro-[1,2,5]-thiadiazino[5,6-a]benzimidazole 1,1-dioxide.
3,4-Dihydro-2H-2-(1-naphthyl)-[1,2,5]-thiadiazino[5,6-a]benzimidazole 1,1-dioxide.
3,4-Dihydro-2H-2-ethyl-7-trifluoromethyl-[1,2,5]-thiadiazino[5,6-a]benzimidazole 1,1-dioxide.
3,4-Dihydro-2H-2-ethyl-8-trifluoromethyl-[1,2,5]-thiadiazino[5,6-a]benzimidazole 1,1-dioxide.
2H-2-(1-Adamantyl)-3,4-dihydro-[1,2,5]-thiadiazino[5,6-a]benzimidazole 1,1-dioxide.
7-Benzoyl-3,4-dihydro-2H-2-ethyl-[1,2,5]-thiadiazino[5,6-a]benzimidazole 1,1-dioxide.
8-Benzoyl-3,4-dihydro-2H-2-ethyl-[1,2,5]-thiadiazino[5,6-a]benzimidazole 1,1-dioxide.
3,4-Dihydro-2H-2-(4-methoxybenzyl)-[1,2,5]-thiadiazino[5,6-a]benzimidazole 1,1-dioxide.
3,4-Dihydro-2H-2-(2-pyridylmethyl)-[1,2,5]-thiadiazino[5,6-a]benzimidazole 1,1-dioxide.
3,4-Dihydro-2H-2-[2-(2-pyridylethyl)]-[1,2,5]-thiadiazino[5,6-a]benzimidazole 1,1-dioxide.
8-Chloro-3,4-dihydro-2H-2-cyclohexyl-[1,2,5]-thiadiazino[5,6-a]benzimidazole 1,1-dioxide.
7-Chloro-3,4-dihydro-2H-2-cyclohexyl-[1,2,5]-thiadiazino[5,6-a]benzimidazole 1,1-dioxide.
2-(2-Diethylamino-1-ethyl)-3,4-dihydro-2H-[1,2,5]-thiadiazino[5,6-a]benzimidazole 1,1-dioxide.
8-Chloro-3,4-dihydro-2H-[1,2,5]-thiadiazino[5,6-a]benzimidazole 1,1-dioxide.
7-Chloro-3,4-dihydro-2H-[1,2,5]-thiadiazino[5,6-a]benzimidazole 1,1-dioxide.
7,8-Dichloro-3,4-dihydro-2H-[1,2,5]-thiadiazino[5,6-a]benzimidazole 1,1-dioxide.
2-Butyl-7,8-dichloro-3,4-dihydro-2H-9-nitro-[1,2,5]-thiadiazino[5,6-a]benzimidazole 1,1-dioxide.
3,4-Dihydro-2H-2-ethyl-7-nitro-[1,2,5]-thiadiazino[5,6-a]benzimidazole 1,1-dioxide.
3,4-Dihydro-2H-2-ethyl-8-nitro-[1,2,5]-thiadiazino[5,6-a]benzimidazole 1,1-dioxide.
3,4-Dihydro-2H-2-methyl-7-nitro-[1,2,5]-thiadiazino[5,6-a]benzimidazole 1,1-dioxide.
3,4-Dihydro-2H-2-methyl-8-nitro-[1,2,5]-thiadiazino[5,6-a]benzimidazole 1,1-dioxide.
3,4,5-Trihydro-2H-2-ethyl-8-nitro-[1,2,6]-thiadiazepino[6,7-a]benzimidazole 1,1-dioxide.
3,4,5-Trihydro-2H-2-ethyl-9-nitro-[1,2,6]-thiadiazepino[6,7-a]benzimidazole 1,1-dioxide.
2H-2-Butyl-3,4-dihydro-7-nitro-[1,2,5]-thiadiazino[5,6-a]benzimidazole 1,1-dioxide.
2H-2-Butyl-3,4-dihydro-8-nitro-[1,2,5]-thiadiazino[5,6-a]benzimidazole 1,1-dioxide.
3,4-Dihydro-2H-8-nitro-2-[2-(2-pyridylethyl)]-[1,2,5]-thiadiazino[5,6-a]benzimidazole 1,1-dioxide.
3,4-Dihydro-2H-7-nitro-2-[2-(2-pyridylethyl)]-[1,2,5]-thiadiazino[5,6-a]benzimidazole 1,1-dioxide.
3,4-Dihydro-2H-8-nitro-(2-pyridylmethyl)-[1,2,5]-thiadiazino[5,6-a]benzimidazole 1,1-dioxide.
3,4-Dihydro-2H-7-nitro-(2-pyridylmethyl)-[1,2,5]-thiadiazino[5,6-a]benzimidazole 1,1-dioxide.
3,4,5,6-Tetrahydro-2H-2-ethyl-9-nitro-[1,2,7]-thiadiazozino[7,8-a]benzimidazole 1,1-dioxide.
3,4,5,6-Tetrahydro-2H-2-ethyl-10-nitro-[1,2,7]-thiadiazozino[7,8-a]benzimidazole 1,1-dioxide.
3,4-Dihydro-2H-2-[3-(4-morpholinopropyl)]-7-nitro[1,2,5]-thiadiazino[5,6-a]benzimidazole 1,1-dioxide.
3,4-Dihydro-2H-2-[3-(4-morpholinopropyl)]-8-nitro[1,2,5]-thiadiazino[5,6-a]benzimidazole 1,1-dioxide.
2H-2-(4-Diethylamino-1-methylbutyl)-3,4-dihydro-7-nitro-[1,2,5]-thiadiazino[5,6-a]benzimidazole 1,1-dioxide.
2H-2-(4-Diethylamino-1-methylbutyl)-3,4-dihydro-8-nitro-[1,2,5]-thiadiazino[5,6-a]benzimidazole 1,1-dioxide.
3,4-Dihydro-2H-7-nitro-[1,2,5]-thiadiazino[5,6-a]benzimidazole 1,1-dioxide.
3,4-Dihydro-2H-8-nitro-[1,2,5]-thiadiazino[5,6-a]benzimidazole 1,1-dioxide.
2H-2-(1-Adamantyl)-3,4-dihydro-7-nitro-[1,2,5]-thiadiazino[5,6-a]benzimidazole 1,1-dioxide.
2H-2-(1-Adamantyl)-3,4-dihydro-8-nitro-[1,2,5]-thiadiazino[5,6-a]benzimidazole 1,1-dioxide.
7-Amino-3,4-dihydro-2H-2-ethyl-[1,2,5]-thiadiazino[5,6-a]benzimidazole 1,1-dioxide.
3,4-Dihydro-2H-2-ethyl-7-isothiocyanato-[1,2,5]-thiadiazino[5,6-a]benzimidazole 1,1-dioxide.
7-Acetylamino-3,4-dihydro-2H-2-ethyl-[1,2,5]-thiadiazino[5,6-a]benzimidazole 1,1-dioxide.
2-Carboxyethylmethyl-8-chloro-3,4-dihydro-2H-[1,2,5]-thiadiazino[5,6-a]benzimidazole 1,1-dioxide.
2-Carboxyethylmethyl-7-chloro-3,4-dihydro-2H-[1,2,5]-thiadiazino[5,6-a]benzimidazole 1,1-dioxide.
8-Chloro-2-(6-chloro-1-hexyl)-3,4-dihydro-2H-[1,2,5]-thiadiazino[5,6-a]benzimidazole 1,1-dioxide.
7-Chloro-2-(6-chloro-1-hexyl)-3,4-dihydro-2H-[1,2,5]-thiadiazino[5,6-a]benzimidazole 1,1-dioxide.
8-Chloro-2-(2-chloro-1-ethyl)-3,4-dihydro-2H-[1,2,5]-thiadiazino[5,6-a]benzimidazole 1,1-dioxide.
7-Chloro-2-(2-chloro-1-ethyl)-3,4-dihydro-2H-[1,2,5]-thiadiazino[5,6-a]benzimidazole 1,1-dioxide.
2-(3-Chloro-1-propyl)-3,4-dihydro-2H-7-nitro-[1,2,5]-thiadiazino[5,6-a]benzimidazole 1,1-dioxide.
8-Chloro-2-(4-cyano-1-butyl)-3,4-dihydro-2H-[1,2,5]-thiadiazino[5,6-a]benzimidazole 1,1-dioxide.
7-Chloro-2-(4-cyano-1-butyl)-3,4-dihydro-2H-[1,2,5]-thiadiazino[5,6-a]benzimidazole 1,1-dioxide.
2-{3-[N-methyl-N-[2-(3,4-dimethoxyphenyl)ethyl]]-propylamino}-3,4-dihydro-2H-7-nitro-[1,2,5]-thiadiazino[5,6-a]benzimidazole 1,1-dioxide.
8-Chloro-2-(6-diethylamino-1-hexyl)-3,4-dihydro-2H-[1,2,5]-thiadiazino[5,6-a]benzimidazole 1,1-dioxide.
7-Chloro-2-(6-diethylamino-1-hexyl)-3,4-dihydro-2H-[1,2,5]-thiadiazino[5,6-a]benzimidazole 1,1-dioxide.
8-Chloro-2-cyanomethyl-3,4-dihydro-2H-[1,2,5]-thiadiazino[5,6-a]benzimidazole 1,1-dioxide.
7-Chloro-2-cyanomethyl-3,4-dihydro-2H-[1,2,5]-thiadiazino[5,6-a]benzimidazole 1,1-dioxide.
8-Chloro-2-(2-diethylamino-1-ethyl)-3,4-dihydro-2H-[1,2,5]-thiadiazino[5,6-a]benzimidazole 1,1-dioxide.
7-Chloro-2-(2-diethylamino-1-ethyl)-3,4-dihydro-2H-[1,2,5]-thiadiazino[5,6-a]benzimidazole 1,1-dioxide.
7-Chloro-2-(6-ethylamino-1-hexyl)-3,4-dihydro-2H-[1,2,5]-thiadiazino[5,6-a]benzimidazole 1,1-dioxide.
7-Chloro-2-(2-pyridyl)-3,4-dihydro-2H-[1,2,5]-thiadiazino[5,6-a]benzimidazole 1,1-dioxide.

3,4-Dihydro-2H-2-ethyl-3-methyl-[1,2,5]-thiadiazino[5,6-a]benzimidazole 1,1-dioxide.

3,4-Dihydro-2H-2-ethyl-3-methyl-7-nitro-[1,2,5]-thiadiazino[5,6-d]benzimidazole 1,1-dioxide.

3,4-Dihydro-2H-2-ethyl-3-methyl-8-nitro-[1,2,5]-thiadiazino[5,6-a]benzimidazole 1,1-dioxide.

2H-2-Butyl-3,4-Dihydropyrido[3',2':4,5]imidazo[1,2-e]-[1,2,5]-thiadiazine 1,1-dioxide.

2-Butyl-3,4-dihydro-2H-pyrido[3',4':4,5]imidazo[1,2-e][1,2,5]-thiadiazine 1,1-dioxide.

1,2,3,4,13,14-Hexahydropyrido[1',2':2,3]-[1,2,5]-thiadiazino[5,6-a]benzimidazole 6,6-dioxide.

1,2,3,4,13,14-Hexahydro-9-nitropyrido[1',2':2,3]-[1,2,5]-thiadiazino[5,6-a]benzimidazole 6,6-dioxide.

1,2,3,4,13,14-Hexahydro-10-nitropyrido[1',2':2,3]-[1,2,5]-thiadiazino[5,6-a]benzimidazole 6,6-dioxide.

2H-2-Ethyl-[1,2,5]-thiadiazino[5,6-a]benzimidazole 1,1-dioxide.

2H-2-Ethyl-3-methyl-[1,2,5]-thiadiazino[5,6-a]benzimidazole 1,1-dioxide.

2H-2-Ethyl-3-phenyl-[1,2,5]-thiadiazino[5,6-a]benzimidazole 1,1-dioxide.

2H-2-Ethyl-7-nitro-3-(4-nitrophenyl)-[1,2,5]-thiadiazino[5,6-a]benzimidazole 1,1-dioxide.

According to the invention, the novel derivatives of the general formula I can be prepared by the following methods:

Method A

Reaction of a suspension, in water or in 10 to 90% aqueous acetic acid, of a compound of the general formula II:

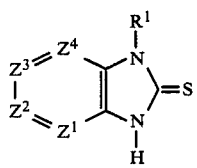

in which:

$Z^1$ represents a nitrogen atom or a carbon atom bonded to another radical $R^4$ (C—$R^4$);

$Z^2$ represents a nitrogen atom or a carbon atom bonded to another radical $R^5$ (C—$R^5$);

$Z^3$ represents a nitrogen atom or a carbon atom bonded to another radical $R^6$ (C—$R^6$);

$Z^4$ represents a nitrogen atom or a carbon atom bonded to another radical $R^7$ (C—$R^7$);

with the restriction that only one of the groups $Z^1$, $Z^2$, $Z^3$ or $Z^4$ can represent a nitrogen atom;

$R^1$ represents a hydrogen atom, a linear or branched alkyl radical, an alkylaryl radical, an alkylcarbonylalkyl radical, an alkylcarbonylaryl radical, an alkylcarbonylheteroaryl radical or a cycloalkyl radical;

$R^4$ and $R^7$ independently represent a hydrogen atom, a halogen atom, a nitro radical, an amino radical or an acylamino radical (such as acetylamino); and $R^5$ and $R^6$ independently represent a hydrogen atom, a halogen atom, an amino radical, a nitro radical, a lower alkyl radical, a trifluoromethyl radical, an alkoxy radical, an aryloxy radical, a mercapto radical, an alkylthio radical, an alkylsulfinyl radical, an alkylsulfonyl radical, a sulfamoyl radical, an isothiocyanate radical, an alkylcarbonyl radical, an arylcarbonyl radical, an acylamino radical (such as acetylamino), a cyano radical, a carboxyl group, a carboxamido group or a carboxyalkyl group;

with a stream of chlorine gas for a period of between 10 minutes and two hours gives the corresponding sulfonyl chloride. The reaction takes place at temperatures of between 0° C. and 15° C., it being possible in certain cases to use a Lewis acid, such as ferric chloride, zinc chloride or tin(IV) chloride, as a catalyst. The acid chloride formed is filtered off and immediately added to a solution, in a suitable solvent such as water, an alcohol, acetone or a mixture thereof, of the compound of the general formula III:

in which:

$R^2$ represents a hydrogen atom or a linear or branched $C_1$ to $C_5$ lower alkyl radical;

$R^3$ represents a hydrogen atom, a linear or branched alkyl radical, an aryl radical, a heteroaryl radical, an alkylaryl radical, an alkylheteroaryl radical, a mono-, bi- or tri-cycloalkyl radical, an alkylamino radical, an N-alkyl-alkylamino radical, an alkylcarboxyalkyl radical, an acyl radical, an alkylthioalkyl, alkylsulfinylalkyl or alkylsulfonylalkyl radical, an alkylthioaryl, alkylsulfinylaryl or alkylsulfonylaryl radical, an alkylthioheteroaryl, alkylsulfinylheteroaryl or alkylsulfonylheteroaryl radical, an alkylthioalkylaryl, alkylsulfinylalkylaryl or alkylsulfonylalkylaryl radical, an alkylthioalkylheteroaryl, alkylsulfinylalkylheteroaryl or alkylsulfonylalkylheteroaryl radical, a halogenalkyl radical, a cyanoalkyl radical, an N-alkylaryl-alkylamino radical, an N-alkyl-N-alkylaryl-alkylamino radical, an N,N-dialkyl-alkylamino radical, a hydroxyalkyl radical, an alkylpiperazinyl radical, an alkylpiperidinyl radical or an alkylmorpholinyl radical;

$R^2$ and $R^3$ can together form a linkage represented by a group —(CH$_2$)$_n$—Y$_m$—CHR$^{10}$—;

Y represents —CH$_2$—O—CH$_2$— or —CH$_2$—NR$^{11}$—CH$_2$—;

n represents 1, 2, 3 or 4;

m represents 0 or 1;

$R^{10}$ represents a hydrogen atom, a hydroxylalkyl radical, a halogenoalkyl radical or a carboxyalkyl radical; and $R^{11}$ represents a hydrogen atom, a lower alkyl radical or a hydroxyalkyl radical.

The reaction takes place at temperatures of between −10° C. and 40° C. for 1 to 4 hours. In the compounds of the general formulae Ia and Ic prepared, $Z^1$, $Z_2$, $Z^3$, $Z^4$, $R^1$ or $R^7$, Y, n, m, $R^{10}$ and $R^{11}$ have the meanings mentioned above.

Method B

Reaction of a compound of the general formula Ia in which $Z^1$, $Z^2$, $Z^3$, $Z^4$ and $R^3$ to $R^7$ have the meanings mentioned above and $R^1$ and $R^2$ represent a hydrogen atom with a compound of the general formula IV or with a compound of the general formula V:

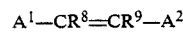

in which:
$A^1$ and $A^2$ independently represent a chlorine atom, a bromine atom or an iodine atom;
$R^8$ and $R^9$ independently represent a hydrogen atom, a lower alkyl radical, an aryl radical or a heteroaryl radical;
n represents 1, 2, 3 or 4; and
m represents 0 or 1.

In the compounds of the general formula Ib prepared, $Z^1$, $Z^2$, $Z^3$, $Z^4$, X and $R^3$ to $R^9$ have the meanings mentioned above.

The reaction takes place in the presence of a suitable solvent, for example dimethyl sulfoxide, an alcohol such as methanol or ethanol, acetone, acetonitrile, an ether such as tetrahydrofuran or dioxane, or a mixture of these solvents with water. This reaction is advantageously carried out in the presence of a suitable base, which can be either an inorganic base such as potassium carbonate, potassium hydroxide or a mixture of the two, or an organic base such as a tertiary or secondary amine. It is possible to use a catalyst selected from the group comprising a quaternary ammonium salt such as benzyltriethylammonium chloride, tetrabutylammonium bromide or tetrabutylammonium bisulfate, or a phosphonium salt such as benzyltriphenylphosphonium chloride or 2-dimethylaminoethyltriphenylphosphonium bromide. The most suitable temperatures vary between about $-5°$ C. and the reflux temperature of the solvent, the reaction time being between 1 hour and 24 hours.

Method C

Reaction of a compound of the general formula Ic in which $Z^1$, $Z^2$, $Z^3$, $Z^4$, Y, n, m, $R^4$ to $R^7$ and $R^{11}$ have the meanings mentioned above, $R^1$ represents a hydrogen atom and $R^{10}$ represents a hydroxymethyl group ($CH_2OH$) with a dehydrating compound such as polyphosphoric acid or thionyl chloride. The most appropriate temperatures vary between 30° C. and 140° C., the reaction time being between 1 hour and 5 hours.

In the compounds of the general formula Id prepared, $Z^1$, $Z^2$, $Z^3$, $Z^4$, Y, n, m, $R^4$ to $R^7$ and $R^{11}$ have the meanings mentioned above.

Method D

Reaction of a compound of the general formula Ia in which $Z^1$, $Z^2$, $Z^3$, $Z^4$, Y, n, m, $R^3$ to $R^7$ and $R^{11}$ have the meanings mentioned above, $R^1$ represents an alkylcarbonylalkyl radical, an alkylcarbonylaryl radical or an alkylcarbonylheteroaryl radical and $R^2$ represents a hydrogen atom with a dehydrating compound such as polyphosphoric acid, thionyl chloride, p-toluenesulfonic acid, titanium tetrachloride or phosphorus oxychloride. The reaction can be carried out in a solvent such as toluene or xylene, or in the absence of a solvent. The most appropriate temperatures vary between 50° C. and 150° C., the reaction time being between 1 hour and 8 hours.

In the compounds of the general formula Ib prepared, $Z^1$, $Z^2$, $Z^3$, $Z^4$, Y, n, m, $R^3$ to $R^7$ and $R^{11}$ have the meanings mentioned above, X represents $-CR^8=CR^9-$, $R^8$ represents a hydrogen atom and $R^9$ represents a lower alkyl radical, an aryl radical or a heteroaryl radical.

Method E

Reaction of a compound of the general formula Ia in which $Z^1$ to $Z^4$ and $R^2$ to $R^7$ have the meanings mentioned above and $R^1$ represents a hydrogen atom with a compound of the general formula VI:

$$A^1-R^1 \qquad \text{VI}$$

in which:
$A^1$ represents a chlorine atom, a bromine atom or an iodine atom; and
$R^1$ represents a linear or branched $C_1$ to $C_5$ alkyl radical, a cycloalkyl radical, an alkylaryl radical, an alkylcarbonylalkyl radical, a carboxyalkyl radical, an alkylcarbonylaryl radical or an alkylcarbonylheteroaryl radical.

The reaction takes place in the presence of an appropriate solvent, for example dimethyl sulfoxide, dimethylformamide, an alcohol, acetone or a mixture of these solvents with water. This reaction is advantageously carried out in the presence of an appropriate base, which can be either an inorganic base such as sodium carbonate, or an organic base such as a tertiary amine. The most appropriate temperatures vary between 20° C. and the reflux temperature of the solvent, the reaction time being between 2 hours and 24 hours.

In the compounds of the general formula Ia prepared, $Z^1$ to $Z^4$ and $R^2$ to $R^7$ have the meanings mentioned above and $R^1$ has the meanings mentioned, except for hydrogen.

Method F

Reaction of a compound of the general formula Ia in which $Z^1$ to $Z^4$ and $R^3$ to $R^7$ have the meanings mentioned above, $R^2$ represents a hydrogen atom and $R^1$ represents a hydrogen atom, a linear or branched $C_1$ to $C_5$ alkyl radical, a cycloalkyl radical, an alkylaryl radical, an alkylcarbonylalkyl radical, a carboxyalkyl radical, an alkylcarbonylaryl radical or an alkylcarbonylheteroaryl radical with a compound of the general formula VII:

$$A^1-R^2 \qquad \text{VII}$$

in which:
$A^1$ represents a chlorine atom, a bromine atome, an iodine atom or an acyloxy radical; and
$R^2$ represents a linear or branched $C_1$ to $C_5$ lower alkyl radical or an acyl radical.

The reaction takes place in the presence of an appropriate solvent, for example dimethylformamide, an alcohol, acetone or a mixture of these solvents with water. This reaction is advantageously carried out in the presence of an appropriate base such as sodium hydroxide, sodium carbonate or sodium hydride. The most appropriate temperatures vary between 10° C. and 60° C., the reaction time being between 2 hours and 24 hours.

In the compounds of the general formula Ia prepared, $Z^1$ to $Z^4$ and $R^3$ to $R^7$ have the meanings mentioned above and $R^1$ and $R^2$ have the meanings mentioned above, except for hydrogen.

Method G

Reaction of a compound of the general formula Ib in which $Z^1$ to $Z^4$ and $R^4$ to $R^9$ have the meanings mentioned above, X represents $-(CHR^8)_n-(CHR^9)_m-$, n3 represents 1, 2, 3 or 4, m represents 0 or 1 and $R^3$ represents a hydrogen atom with a compound of the general formula VIII:

$$A^1-R^3 \qquad \text{VIII}$$

in which:

$A^1$ represents a fluorine atom, a chlorine atom, a bromine atom or an iodine atom; and $R^3$ represents a linear or branched alkyl radical, a heteroaryl radical, an alkylaryl radical, an alkylheteroaryl radical, a mono-, bi- or tri-cycloalkyl radical, an alkylamino radical, an N-alkyl-alkylamino radical, an alkylcarboxyalkyl radical, an acyl radical, an alkylthioalkyl, alkylsulfinylalkyl or alkylsulfonylalkyl radical, an alkylthioaryl, alkylsulfinylaryl or alkylsulfonylaryl radical, an alkylthioheteroaryl, alkylsulfinylheteroaryl or alkylsulfonylheteroaryl radical, an alkylthioalkylaryl, alkylsulfinylalkylaryl or alkylsulfonylalkylaryl radical, an alkylthioalkylheteroaryl, alkylsulfinylalkylheteroaryl or alkylsulfonylalkylheteroaryl radical, a halogenoalkyl radical, a cyanoalkyl radical, an N-alkylaryl-alkylamino radical, an N-alkyl-N-alkylarylalkylamino radical, an N,N-dialkyl-alkylamino radical, a hydroxyalkyl radical, an alkylpiperazinyl radical, an alkylpiperidinyl radical or an alkylmorpholinyl radical.

The reaction takes place in the presence of an appropriate solvent, for example dimethyl sulfoxide, dimethylformamide, an alcohol, acetone or a mixture of these solvents with water. This reaction is advantageously carried out in the presence of an appropriate base, which can be either an inorganic base such as sodium hydride, potassium carbonate, potassium hydroxide or a mixture of these last two, or an organic base such as a tertiary amine. It is possible to use a catalyst selected from the group comprising a quaternary ammonium salt or a phosphonium salt. The most appropriate temperatures vary between about $-5°$ C. and the reflux temperature of the solvent, the reaction time being between 1 hour and 24 hours.

In the compounds of the general formula Ib prepared, $Z^1$ to $Z^4$ and $R^4$ to $R^9$ have the meanings mentioned above and $R^3$ has the meanings mentioned above, except for hydrogen.

Method H

Nitration of a compound of the general formula I in which $Z^1$ represents $C-R^4$, $Z^2$ represents $C-R^5$, $Z^3$ represents $C-R^6$, $Z^4$ represents $C-R^7$, one of the two radicals $R^5$ and $R^6$ represents a hydrogen atom and the other represents a hydrogen atom, a halogen atom, a nitro radical, a lower alkyl radical, a trifluoromethyl radical, an alkoxy radical, an aryloxy radical or an acylamino radical and $R^1$ to $R^4$, $R^7$ to $R^{11}$, X, Y, n and m have the meanings mentioned above with a nitrating agent such as a mixture of nitric acid and another strong acid, for example sulfuric acid, or with nitronium tetrafluoroborate.

The reaction takes place without a solvent or with an appropriate solvent such as tetramethylenesulfone. The most appropriate temperatures vary between $-10°$ C. and $120°$ C., the reaction time being between 15 minutes and 6 hours.

In the compounds of the general formula I prepared, $Z^1$ represents $C-R^4$, $Z^2$ represents $C-R^5$, $Z^3$ represents $C-R^6$, $Z^4$ represents $C-R^7$, one of the two radicals $R^5$ and $R^6$ represents a nitro group and the other represents a hydrogen atom, a halogen atom, a nitro radical, a lower alkyl radical, a trifluoromethyl radical, an alkoxy radical, an aryloxy radical or an acylamino radical and $R^1$ to $R^4$, $R^7$, to $R^{11}$, X, Y, n and m have the meanings mentioned above.

Method J

Reduction of a compound of the general formula I in which $Z^1$ represents $C-R^4$, $Z^2$ represents $C-R^5$, $Z^3$ represents $C-R^6$, $Z^4$ represents $C-R^7$, one of the four radicals $R^4$, $R^5$, $R^6$ or $R^7$ represents a nitro group and the others represent a hydrogen atom and $R^1$ to $R^3$, $R^8$ to $R^{11}$, X, Y, n and m have the meanings mentioned above with a suitable reducing agent.

The following may be mentioned among the numerous reducing agents which can be used to reduce a nitro group to an amino group: catalytic hydrogenation using Raney nickel or palladium-on-carbon, sodium sulfide, ammonium sulfide, ferrous sulfate/ammonium hydroxide, zinc/ammonium acetate, zinc amalgam/hydrochloric acid, etc. as the catalyst. The reaction takes place in an alcohol such as methanol or ethanol, or alternatively a mixture of an alcohol with water. The most suitable temperatures vary between $10°$ C. and $60°$ C., the reaction time being between 2 hours and 24 hours.

In the compounds of the general formula I prepared, $Z^1$ represents $C-R^4$, $Z^2$ represents $C-R^5$, $Z^3$ represents $C-R^6$, $Z^4$ represents $C-R^7$, one of the four radicals $R^4$, $R^5$, $R^6$ or $R^7$ represents an amino group and the others represent a hydrogen atom and $R^1$ to $R^3$, $R^8$ to $R^{11}$, X, Y, n and m have the meanings mentioned above.

Method K

Acylation of a compound of the general formula I in which $Z^1$ represents $C-R^4$, $Z^2$ represents $C-R^5$, $Z^3$ represents $C-R^6$, $Z^4$ represents $C-R^7$, one of the four radicals $R^4$, $R^5$, $R^6$ or $R^7$ represents an amino group and the others represent a hydrogen atom and $R^1$ to $R^3$, $R^8$ to $R^{11}$, X, Y, n and m have the meanings mentioned above with an acid halide or an anhydride.

The reaction takes place without a solvent or with an appropriate solvent such as a tertiary amine, for example pyridine. The most appropriate temperatures vary between $0°$ C. and $60°$ C., the reaction time being between 1 hour and 12 hours.

In the compounds of the general formula I prepared, $Z^1$ represents $C-R^4$, $Z^2$ represents $C-R^5$, $Z^3$ represents $C-R^6$, $Z^4$ represents $C-R^7$, one of the four radicals $R^4$, $R^5$, $R^6$ or $R^7$ represents an acylamino group and the others represent a hydrogen atom and $R^1$ to $R^3$, $R^8$ to $R^{11}$, X, Y, n and m have the meanings mentioned above.

Method L

Reaction of a compound of the general formula I in which $Z^1$ represents $C-R^4$, $Z^2$ represents $C-R^5$, $Z^3$ represents $C-R^6$, $Z^4$ represents $C-R^7$, one of the four radicals $R^4$, $R^5$, $R^6$ or $R^7$ represents an amino group and the others represent a hydrogen atom and $R^1$ to $R^3$, $R^8$ to $R^{11}$, X, Y, n and m have the meanings mentioned above with thiophosgene ($Cl_2CS$).

The reaction takes place in a mixture of hydrochloric acid and a solvent which is preferably chlorinated, such as chloroform. The most appropriate temperatures vary between $10°$ C. and the reflux temperature of the solvent, the reaction time being between 6 hours and 24 hours.

In the compounds of the general formula I prepared, $Z^1$ represents $C-R^4$, $Z^2$ represents $C-R^5$, $Z^3$ represents $C-R^6$, $Z^4$ represents $C-R^7$, one of the four radicals $R^4$, $R^5$, $R^6$ or $R^7$ represents an isothiocyanate group ($-N=C=S$) and the others represent a hydrogen atom and $R^1$ to $R^3$, $R^8$ to $R^{11}$, X, Y, n and m have the meanings mentioned above.

Method M

Reaction of a compound of the general formula I in which $Z^1$ represents C—$R^4$, $Z^2$ represents C—$R^5$, $Z^3$ represents C—$R^6$, $Z^4$ represents C—$R^7$, one of the four radicals $R^4$, $R^5$, $R^6$ or $R^7$ represents an amino group and the others represent a hydrogen atom and $R^1$ to $R^3$, $R^8$ to $R^{11}$, X, Y, n and m have the meanings mentioned above with sodium nitrite in an aqueous solution of hydrochloric or tetrafluoroboric acid or in acetic acid saturated with hydrogen chloride, at a temperature of between $-10°$ C. and $5°$ C., gives the corresponding diazonium salt, which is poured into an aqueous solution of cuprous chloride or cuprous cyanide or alternatively into a solution of acetic acid saturated with sulfur dioxide and a catalytic amount of cuprous chloride and cupric chloride. In the latter case, the sulfonyl chloride obtained is reacted with aqueous ammonia under the usual conditions for the formation of a sulfamide. The corresponding solutions are kept at between $5°$ C. and room temperature for periods varying between 1 hour and 4 hours.

In the compounds of the general formula I prepared, $Z^1$ represents C—$R^4$, $Z^2$ represents C—$R^5$, $Z^3$ represents C—$R^6$, $Z^4$ represents C—$R^7$, one of the four radicals $R^4$, $R^5$, $R^6$ or $R^7$ represents a chlorine atom, a cyano group (—C≡N) or a sulfamoyl group (—$SO_2NH_2$) and the others represent a hydrogen atom and $R^1$ to $R^3$, $R^8$ to $R^{11}$, X, Y, n and m have the meanings mentioned above.

For the compounds of the general formula I in which $Z^1$ is different from $Z^4$ or $Z^2$ is different from $Z^3$ and $R^1$ is different from hydrogen, two position isomers are obtained in certain cases, and these can be separated by fractional crystallization or by chromatographic methods.

The compounds of the general formula I according to the invention can be synthesized either in the form of the free base or in the form of a salt, according to the reaction conditions and the nature of the starting materials. The salts can be converted to the free base using basic agents such as alkalis and alkali metal carbonates, or by ion exchange. On the other hand, the free bases synthesized can in turn form salts with mineral or organic acids.

The compounds of the general formulae II or VIII are known or can be prepared by processes analogous to known processes starting from readily accessible compounds. The compounds of the general formula II are known or can be prepared, by the methods described in the chemical literature [J. A. Van Allan and B. D. Deacon, Organic Syntheses, Coll. Vol. IV, p. 569, and the references cited therein], from the corresponding diamines of the general formula IX:

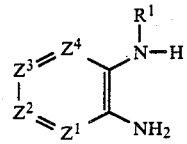

in which:
$Z^1$ represents a nitrogen atom or a carbon atom bonded to another radical $R^4$ (C—$R^4$);
$Z^2$ represents a nitrogen atom or a carbon atom bonded to another radical $R^5$ (C—$R^5$);
$Z^3$ represents a nitrogen atom or a carbon atom bonded to another radical $R^6$ (C—$R^6$);
$Z^4$ represents a nitrogen atom or a carbon atom bonded to another radical $R^7$ (C—$R^7$);
with the restriction that only one of the groups $Z^1$, $Z^2$, $Z^3$ or $Z^4$ can represent a nitrogen atom; and
$R^1$ represents a hydrogen atom, a linear or branched alkyl radical, an alkylaryl radical, an alkylcarbonylalkyl radical, an alkylcarbonylaryl radical, an alkylcarbonylheteroaryl radical or a cycloalkyl radical.

The preparation of novel derivatives according to the invention will be indicated in the examples which follow. Some typical use forms for the various areas of application will also be described.

The examples below are given simply by way of illustration and are not intended to limit the scope of the invention in any way.

EXAMPLE 1

Method A

Preparation of 5-benzoyl-N-ethyl-1H-benzimidazole-2-sulfonamide

Chlorine is bubbled for one hour into a suspension of 50.9 g (0.2 mol) of 2-mercapto-5-benzoyl-1H-benzimidazole in 1200 ml of 20% aqueous acetic acid in such a way that the temperature does not exceed $7°$ C. The acid chloride obtained is filtered off, washed with cold water and immediately added in small portions to 200 ml of 17% aqueous ethylamine cooled to $5°$ C. beforehand. The mixture is stirred until it reaches room temperature, and stirring is then continued for 1 hour. The solution is adjusted to pH 5 with hydrochloric acid and the product is filtered off and washed with water. Recrystallization from ethyl acetate gives 51.3 g (78%) of 5-benzoyl-N-ethyl-1H-benzimidazole-2-sulfonamide melting at $250°-3°$ C.

The data for identifying the product are given in Tables 1 and 2.

TABLE 1

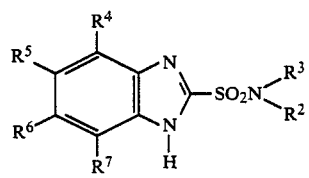

| Example no | $R^2$ | $R^3$ | $R^4$ | $R^5$ | $R^6$ | $R^7$ | M.p. (°C.) | IR (KBr) |
|---|---|---|---|---|---|---|---|---|
| 1 | H | —$CH_2CH_3$ | H | $C_6H_5\overset{O}{\underset{\|}{C}}$— | H | H | 250-3 | 1645;1340;1150 |

TABLE 1-continued

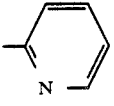

| Example no | R² | R³ | R⁴ | R⁵ | R⁶ | R⁷ | M.p. (°C.) | IR (KBr) |
|---|---|---|---|---|---|---|---|---|
| 2 | H | H | H | H | H | H | 211–3 | 1345;1150 |
| 3 | H | —CH₃ | H | H | H | H | 196–7 | 1350;1165 |
| 4 | H | —CH₂CH₃ | H | H | H | H | 215–8 | 1330;1150 |
| 5 | H | 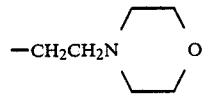 (2-pyridyl) | H | H | H | H | 259–60 | 1285;1175 |
| 6 | H | —CH₂CH₂N(morpholino) 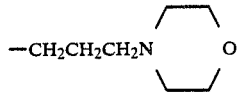 | H | H | H | H | 180–3 | 1340;1160 |
| 7 | H | —CH₂CH₂CH₂CH₂NH₂ | H | H | H | H | 198–203 | 1330;1140 |
| 8 | H | —CH₂CH₂CH₂N(morpholino) 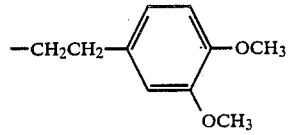 | H | H | H | H | 171–4 | 1355;1155 |
| 9 | H | —CH₂CH₃ | H | Cl | H | H | 219–220 | 1335;1150 |
| 10 | H | —CH₂CH₃ | H | C₆H₅O— | H | H | 253–8 | 1340;1155 |
| 11 | H | —CH₂CH₂-(3,4-dimethoxyphenyl) 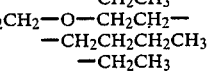 | H | H | H | H | 95–99 | 1345;1155 |
| 12 | —CH₂CH₃ | —CH₂CH₃ | H | H | H | H | 127–9 | 1370;1150 |
| 13 | —CH₂CH₂—O—CH₂CH₂— | | H | H | H | H | 162–9 | 1380;1160 |
| 14 | H | —CH₂CH₂CH₂CH₃ | H | H | H | H | 180–5 | 1350;1160 |
| 15 | H | —CH₂CH₃ | Cl | —CH₃ | —CH₃ | Cl | 310–2 | 1335;1150 |
| 16 | H | 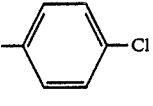 (4-Cl-phenyl) | H | Cl | H | H | 235–7 | 1355;1155 |
| 17 | H | 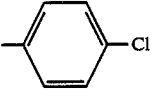 (4-Cl-phenyl) | H | H | H | H | 233–7 | 1360;1160 |
| 18 | H | —CH(CH₃)(CH₂)₃N(CH₂CH₃)₂ | H | Cl | H | H | 219–22 | 1320;1130 |
| 19 | H | —CH₂CH₃ | Cl | —CH₃ | —CH₃ | H | 253–5 | 1350;1160 |
| 20 | H | H | NO₂ | H | H | H | >300 | 1520;1370;1338;1160 |
| 21 | H | —CH₂CH₃ | NO₂ | H | H | H | 204–5 | 1530;1360;1350;1170 |
| 22 | H | —CH(CH₃)(CH₂)₃N(CH₂CH₃)₂ | H | H | H | H | 183–4 | 1310;1135 |
| 23 | H | —CH₂CN | H | H | H | H | 195–7 | 2045;1370;1160 |
| 24 | H | Cyclohexyl | H | H | H | H | 238–40 | 1360;1155 |
| 25 | H | 1-Naphthyl | H | H | H | H | 212–8 | 1330;1145 |
| 26 | H | —CH₂CH₃ | H | —CF₃ | H | H | 221–2 | 1335;1150 |
| 27 | H | 1-Adamantyl | H | H | H | H | 236–46 | 1335;1150 |

TABLE 1-continued

Structure: benzimidazole with R4, R5, R6, R7 on ring, and 2-position has -SO2N(R3)(R2), with NH on imidazole.

| Example no | R² | R³ | R⁴ | R⁵ | R⁶ | R⁷ | M.p. (°C.) | IR (KBr) |
|---|---|---|---|---|---|---|---|---|
| 28 | \-CH₂CH₂CH₂CH₂CH\- (ring closing to R³ side, with CH₂OH on terminal CH) | | H | H | H | H | 175-6 | 1335;1150 |
| 29 | H | —CH₂—C₆H₄—OCH₃ (p-methoxybenzyl) | H | H | H | H | 206-9 | 1335;1145 |
| 30 | H | —(3-methyl-5-isoxazolyl with CH₃) | H | H | H | H | 195-8 | 1355;1160 |
| 31 | H | —CH₂-(2-pyridyl) | H | H | H | H | 212-3 | 1360;1160 |
| 32 | H | —CH₂CH₂-(2-pyridyl) | H | H | H | H | 200-2 | 1345;1160 |
| 33 | H | —CH(CH₂)₃N(CH₂CH₃)₂ / CH₃ | H | C₆H₅C(O)— | H | H | 236-40 | 1650;1320;1135 |
| 34 | H | H | H | NO₂ | H | H | >300 | 1535;1350;1145 |
| 35 | H | —CH₂CH₃ | H | NO₂ | H | H | 240-5 | 1525;1345;1155 |
| 36 | H | —CH₂CH₂N(morpholino) | H | NO₂ | H | H | 208-10 | 1515;1365;1320;1150 |
| 37 | —CH₂CH₃ | —CH₂CH₃ | H | NO₂ | H | H | 135-7 | 1520;1350;1145 |
| 38 | H | —CH₂CH₂CH₂N(morpholino) | H | NO₂ | H | H | 219-22 | 1500;1370;1330;1140 |
| 39 | H | —CH₂CH₂CH₂CH₃ | NO₂ | H | H | H | 181-3 | 1535;1360;1175 |
| 40 | H | —CH₂CH₂OH | NO₂ | H | H | H | 173-5 | 1530;1350;1340;1155 |
| 41 | H | —CH₂CO₂CH₂CH₃ | NO₂ | H | H | H | 167-9 | 1750;1545;1370;1350;1190 |
| 42 | NO₂ | CH₂CH₃ | NO₂ | H | H | H | 149-50 | 1595;1535;1400;1390;1350;1185 |
| 43 | H | —CH₂CH₂N(morpholino) | NO₂ | H | H | H | 172-6 | 1535;1330;1160 |
| 44 | —COCH₃ | —CH₂CH₃ | NO₂ | H | H | H | 166-8 | 1710;1525;1380;1340;1180 |
| 45 | H | —COCH₃ | NO₂ | H | H | H | >320 | 1730;1520;1370;1340;1180 |
| 46 | —CH₂—CH₂—N(—CH₂—CH₂—)₂ with CH₂CH₂OH on N | | NO₂ | H | H | H | 175-7 | 1350;1160 |

TABLE 1-continued

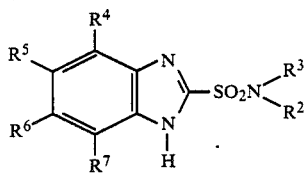

| Example no | R² | R³ | R⁴ | R⁵ | R⁶ | R⁷ | M.p. (°C.) | IR (KBr) |
|---|---|---|---|---|---|---|---|---|
| 47 | H | 4-fluorophenyl | NO₂ | H | H | H | 217–27 | 1535;1370;1345;1180 |
| 48 | —CH₂—CH₂—CH₂—CH(CO₂CH₃)— | | NO₂ | H | H | H | 167–8 | 1735;1535;1355;1345; 1150 |
| 49 | H | —CH₃ | NO₂ | H | H | H | 215–7 | 1535;1335;1170 |
| 50 | H | —CH₂CH₂CH₃ | NO₂ | H | H | H | 190–2 | 1535;1360;1180 |
| 51 | H | —CH(CH₃)—CH₃ | NO₂ | H | H | H | 218–20 | 1545;1340;1180 |
| 52 | H | —CH₂CH₂—S—CH₂—CH₃ | NO₂ | H | H | H | 165–6 | 1535;1355;1175 |
| 53 | H | —CH₂CH₂—S(=O)₂—CH₂—CH₃ | NO₂ | H | H | H | 162–5 | 1540;1360;1175 |
|  | H | 3-methyl-2-oxo-azepan-3-yl | NO₂ | H | H | H | 242–3 | 1650;1535;1340;1175 |
|  | H | —CH(CO₂—CH₂—CH₃)—CH₂—CH₂—CO₂—CH₂—CH₃ | NO₂ | H | H | H | 167–70 | 1740;1720;1535;1375; 1340;1185 |
|  | —CH₂—CH₂—N(CH₃)—CH₂CH₂— | | H | H | H | H | 208–10 | 1350;1150 |
|  | H | Cyclohexyl | H | Cl | H | H | 242–4 | 1350;1190 |
|  | H | —CH₂—CH₂—N(CH₂—CH₃)₂ | H | H | H | H | 180–2 | 1320;1150 |

TABLE 2

| Example no | ¹H NMR (DMSO-d₆) δ |
|---|---|
| 1 | 1,09(t,3H); 3,14(quint.,2H); 7,70(m,7H); 8,04(s,1H); 8,41(t,1H); 13,86(b,1H) |
| 2 | 7,27(m,2H); 7,60(m,2H); 8,03(b,2H); 10,92(b,1H) |
| 3 | 2,75(s,3H); 7,27(m,2H); 7,58(m,2H); 9,60(b,2H) |
| 4 | 1,10(t,3H); 3,13(quint.,2H); 7,33(m,2H); 7,66(m,2H); 8,24(t,1H); 10,52(b,1H) |
| 5 | 6,98(m,3H); 7,19(dd,1H); 7,51(m,2H); 7,81(m,1H); 9,34(dd,1H); 12,30(b,2H) |
| 6 | 2,57(t,4H); 2,72(t,2H); 3,51(t,2H); 3,72(t,4H); 7,60(m,2H); 7,93(m,2H); 9,60(b,2H) |
| 7 | 1,52(m,4H); 2,88(m,4H); 6,65(m,4H); 7,11(m,2H); 7,60(m,2H) |
| 8 | 1,59(quint.,2H); 2,24(m,6H); 3,12(t,2H); 3,48(m,4H); 7,32(m,2H); 7,67(m,2H); 10,55(b,2H) |
| 9 | 1,05(t,3H); 3,10(quint.,2H); 7,35(dd,1H); 7,67(d,1H); 7,71(d,1H); 8,30(t,1H); 13,69(b,1H) |
| 10 | 1,08(t,3H); 3,12(quint.,2H); 6,90(m,2H); 7,28(m,5H); 7,61(d,1H); 8,38(t,1H); 13,90(b,1H) |
| 11 | 2,70(t,2H); 3,34(t,2H); 3,69(s,6H); 6,80(m,3H); 7,38(m,2H); 7,69(m,2H); 8,42(b,1H); 13,60(b,1H) |
| 12 | 1,11(t,6H); 3,36(q,4H); 7,34(m,2H); 7,67(m,2H); 12,50(b,1H) |
| 13 | 3,25(t,4H); 3,71(t,4H); 7,38(m,2H); 7,72(m,2H); 12,75(b,1H) |
| 14 | 0,80(t,3H); 1,42(m,4H); 3,10(q,2H); 7,31(m,2H); 7,67(m,2H); 8,24(t,1H); 13,10(b,1H) |
| 15 | 1,10(t,3H); 2,32(s,6H); 3,12(quint.,2H); 8,30(t,1H); 13,20(b,1H) |
| 16 | 7,28(m,5H); 7,53(m,2H); 12,20(b,2H); |
| 17 | 7,10(m,6H); 7,43(m,2H); 10,90(b,2H); |
| 18 | 0,95(d,3H); 1,02(t,6H); 1,35(m,4H); 2,42(q,4H); 2,48(t,2H); 3,46(sext.,1H); 7,29(dd,1H); 7,64(d,1H); 7,65(d,1H); 9,18(b,2H) |
| 19 | 1,51(t,3H); 2,82(s,6H); 3,55(quint.,2H); 7,75(s,1H); 8,80(t,1H); 14,10(b,1H) |
| 20 | 7,58(t,1H); 8,22(m,4H); 10,20(b,1H); |
| 21 | 1,10(t,3H); 3,14(quint.,2H); 7,47(t,1H); 8,10(m,2H); 8,34(t,1H); 12,50(b,1H) |

TABLE 2-continued

| Example no | $^1$H NMR (DMSO-$d_6$) δ |
|---|---|
| 22 | 0,86(t,6H); 1,05(d,3H); 1,33(,4H); 2,26(q,4H); 2,37(t,2H); 3,46(sext.,1H); 7,28(m,2H); 7,62(m,2H); 9,27(b,2H) |
| 23 | 4,30(s,2H); 7,24(m,2H); 7,59(m,2H); 9,10(b,1H); 13,10(b,1H) |
| 24 | 1,30(m,10H); 3,26(b,1H); 7,31(m,2H); 7,67(m,2H); 8,97(b,1H); 13,51(b,1H) |
| 25 | 7,15-8,27(m,11H); 13,40(b,2H) |
| 26 | 1,06(t,3H); 3,13(quint.,2H); 7,62(dd,1H); 7,86(d,1H); 8,04(d,1H); 8,40(t,1H); 13,97(b,1H) |
| 27 | 1,49(b,6H); 1,82(b,6H); 1,89(b,3H); 7,29(m,2H); 7,66(m,2H); 7,98(s,1H); 13,20(b,1H) |
| 28 | 1,38(m,6H); 3,07(m,1H); 3,45(b,1H); 3,58(d,2H); 3,88(m,2H); 7,32(m,2H); 7,67(m,2H); 12,60(b,1H) |
| 29 | 3,66(s,3H); 4,25(d,2H); 6,81(d,2H); 7,24(d,2H); 7,36(m,2H); 7,69(m,2H); 8,90(t,1H); 12,10(b,1H) |
| 30 | 2,27(s,3H); 6,10(s,1H); 7,18(m,2H); 7,55(m,2H); 11,20(b,2H) |
| 31 | 4,44(s,2H); 7,33(m,4H); 7,68(m,3H); 8,42(d,1H); 9,09(b,1H); 13,52(b,1H) |
| 32 | 2,97(m,2H); 3,52(t,2H); 7,33(m,4H); 7,62(m,3H); 8,43(m,1H); 8,80(b,1H); 13,52(b,1H) |
| 33 | 0,91(t,6H); 1,09(d,3H); 1,41(m,4H); 2,42(m,6H); 3,53(sext.,1H); 6,90(b,2H); 7,66(m,7H); 8,01(s,1H) |
| 34 | 7,70(d,1H); 8,18(dd,1H); 8,20(s,2H); 8,43(d,1H); 10,57(b,1H) |
| 35 | 1,09(t,3H); 3,13(quint.,2H); 7,71(d,1H); 8,11(dd,1H); 8,43(m,3H) |
| 36 | 2,43(t,4H); 2,55(t,2H); 3,33(t,2H); 3,50(t,4H); 7,86(d,1H); 8,23(dd,1H); 8,61(d,1H); 10,37(b,2H) |
| 37 | 1,11(t,6H); 3,35(q,4H); 7,79(d,1H); 8,16(dd,1H); 8,52(d,1H); 12,60(b,1H) |
| 38 | 1,76(quint.,2H); 2,50(t,6H); 3,27(t,2H); 3,64(t,4H); 7,89(d,1H); 8,27(dd,1H); 8,54(d,1H); 10,37(b,2H) |
| 39 | 0,80 (b,3H); 1,39(m,4H); 3,09(t,2H); 7,53 (t,1H); 8,13(d,1H); 8,20(d,1H); 8,29 (b,2H) |
| 40 | 3,22(t,2H); 3,51(t,2H); 7,46(t,1H); 8;11(d,1H); 8,14(d,1H); 8,44(b,3H) |
| 41 | 1,02(t,3H); 3,94(q,2H); 4,04(s,2H); 7,55(t,1H); 8,16 (d,1H) 8,24(d,1H); 9,02(b,2H) |
| 42 | 1,44(t,3H); 4,40(q,2H); 7,62(t,1H); 8,24(d,1H); 8,32(d,1H); 8,85(b,1H) |
| 43 | 2,33(t,4H); 2,47(t,2H); 3,25(t,2H); 3,39(t,4H); 7,54(t,1H); 8,02(b,2H); 8,14(d,1H); 8,22(d,1H) |
| 44 | 1,30(t,3H); 2,33(s,1H); 2,42(s,3H); 3,94(q,2H); 7,59(t,1H); 8,19(d,1H); 8,27(d,1H) |
| 45 | 2,05(s,3H); 3,59(s,2H); 7,61(t,1H); 8,15(d,1H); 8,28(d,1H) |
| 46 | 2,82(m,6H); 3,50(m,6H); 6,60(b,2H); 7,43(t,1H); 8,12(d,1H); 8,16(d,1H) |
| 47 | 7,21(m,4H); 7,50(t,1H); 8.09(d,1H); 8,19(d,1H) |
| 48 | 1,98(m,4H); 3,59(t,2H); 3,67(s,3H); 4,66(t,1H); 7,56(t,1H); 7,56(t,1H); 8,16(d,1H); 8,23(d,1H); 14,00(b,1H) |
| 49 | 2,74(m,3H); 7,52(t,1H); 8,12(d,1H); 8,19(d,1H); 8,40(b,1H; 12,53(b,1H) |
| 50 | 0,81(t,3H); 1,47(sext.,2H); 3,04(q,2H); 7,52(t,1H); 8,12(d,1H); 8,20(d,1H); 8,39(t,1H); 13,28(b,1H) |
| 51 | 1,07(d,6H); 3,61(quint.,1H); 7,30(t,1H); 8,10(d,1H); 8,17(d,1H); 8,28(d,1H); 13,01(b,1H) |
| 52 | 1,14(t,3H); 2,50(q,2H); 2,70(t,2H); 3,30(q,2H); 7,59(t,1H); 8,19(d,1H); 8,27(d,1H); 8,61(t,1H); 13,32(b,1H) |
| 53 | 1,22(t,3H); 3,15(q,2H); 3,46(m,4H); 7,58(t,1H); 8,18(d,1H); 8,26(d,1H); 8,78(t,1H); 10,31(b,1H) |
| 54 | 1,22(m,2H); 1,74(m,4H); 3,09(m,2H); 3,40(b,1H); 4,43(m,1H); 7,50(t,1H); 7,94(b,1H); 8,22(d,1H); 8,37(d,1H); 14,02(b,1H) |
| 55 | 0,96(t,3H); 1,12(t,3H); 1,99(m,2H); 2,45(t,2H); 3,89(q,2H); 3,95(q,2H); 4,24(b,2H); 7,57(t,1H); 8,14(d,1H); 8,24(d,1H); 9,07(b,1H) |
| 56 | 2,08(s,3H); 2,33(t,4H); 3,25(t,4H); 7,33(m,2H); 7,71(m,2H); 12,70(b,1H) |
| 57 | 1,18(m,4H); 1,63(m,6H); 3,25(m,1H); 7,35(d,1H); 7,68(d,1H); 7,72(s,1H); 8,20(b,2H) |
| 58 | 0,81(t,6H); 2,39(q,4H); 2,45(t,2H); 3,10(t,2H); 7,23(m,2H); 7,58(m,2H); 8,22(b,2H) |

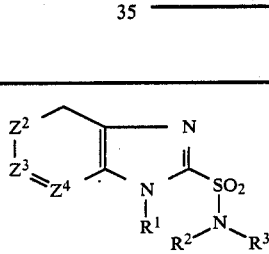

| Example no | $R^1$ | $R^2$ | $R^3$ | $Z^1$ | $Z^2$ | $Z^3$ | $Z^4$ | M.p.(°C.) | IR (KBr) |
|---|---|---|---|---|---|---|---|---|---|
| 59 | H | H | —CH$_2$CH$_3$ | CH | CH | CH | N | 229-30 | 1350;1150 |
| 60 | H | H | —(CH$_2$)$_3$CH$_3$ | CH | CH | CH | N | 222 | 1355;1155 |
| 61 | H | H | —(CH$_2$)$_3$CH$_3$ | CH | CH | N | CH | 185-95 | 1340;1150 |
| 62 | —CH$_2$CH$_3$ | H | —CH$_2$CH$_3$ | CH | CH | CH | CH | 135-9 | 1340;1165 |
| 63 | —CH$_2$CH$_3$ | CH$_2$CH$_3$ | —CH$_2$CH$_3$ | CH | CH | CH | CH | 50-3 | 1330;1150 |
| 64 | —CH$_3$ | —CH$_3$ | —CH$_2$CH$_3$ | CH | CH | CH | CH | 68-74 | 1335;1160 |
| 65 | —CH$_2$$\overset{O}{\overset{\|}{C}}$C$_6$H$_5$ | H | —CH$_2$CH$_3$ | CH | CH | CH | CH | 185-95 | 1690;1355;1165 |
| 66 | —CH$_2$$\overset{O}{\overset{\|}{C}}$CH$_3$ | H | —CH$_2$CH$_3$ | CH | CH | CH | CH | 188-90 | 1735;1355;1165 |
| 67 | —CH$_2$$\overset{O}{\overset{\|}{C}}$C$_6$H$_5$N | H | —CH$_2$CH$_3$ | CH | CH | CH | CH | 170-2 | 1730;1350;1160 |
| 68 | —CH$_2$CH$_3$ | H | —CH(CH$_2$)$_3$N(CH$_2$CH$_3$)$_2$ with CH$_3$ | CH | CCl | CH | CH | | |

-continued

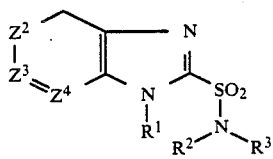

| Example no | R¹ | R² | R³ | Z¹ | Z² | Z³ | Z⁴ | M.p.(°C.) | IR (KBr) |
|---|---|---|---|---|---|---|---|---|---|
| 69 | —CH₂CH₃ | H | CH₃<br>\|<br>—CH(CH₂)₃N(CH₂CH₃)₂ | CH | CH | CCl | CH | 60–71 | 1340;1160 |
| 70 | —CH₂CH₃ | H | —CH₂CH₃ | CNO₂ | CH | CH | CH | 128–30 | 1530;1360;1330;1165 |
| 71 | —CH₂CH₃ | CH₂CH₃ | —CH₂CH₃ | CH | CH | CNO₂ | CH | 90–1 | 1520;1360;1340;1155 |
| 72 | —CH₂CH₃ | CH₂CH₃ | —CH₂CH₃ | CH | CNO₂ | CH | CH | 85–100 | 1525;1345;1150 |
| 73 | —CH₂CH₃ | CH₂CH₃ | CH₃<br>\|<br>—CH(CH₂)₃N(CH₂CH₃)₂ | CH | CCl | CH | CH | | |
| 74 | —CH₂CH₃ | CH₂CH₃ | CH₃<br>\|<br>—CH(CH₂)₃N(CH₂CH₃)₂ | CH | CH | CCl | CH | 35–43 | 1340;1150 |
| 75 | —CH₂CH₃ | CH₂CH₃ | —CH₂CH₃ | CNO₂ | CH | CH | CH | 59–60 | 1530;1335;1150 |
| 76 | —CH₂CH₃ | CH₂CH₃ | —CH₂CH₃ | CH | CH | CH | CNO₂ | 125–7 | 1530;1340;1155 |
| 77 | —CH₂CH₃ | HNO₂ | —CH₂CH₃ | CH | CNO₂ | CH | CH | 108–9 | 1590;1525;1350;1180 |
| 78 | —CH₂CH₃ | HNO₂ | —CH₂CH₃ | CH | CH | CNO₂ | CH | 144–5 | 1590;1525;1350;1185 |
| 79 | —CH₂CH₃ | H | —CH₂CH₃ | CH | CNO₂ | CH | CH | 127–35 | 1520;1350;1165 |
| 80 | —CH₂CH₃ | H | —CH₂CH₃ | CH | CH | CNO₂ | CH | 156–9 | 1525;1350;1170 |
| 81 | H | H | H | CH | CNH₂ | CH | CH | 235–7 | 1350;1150 |
| 82 | H | H | H | CNH₂ | CH | CH | CH | 192–5 | 1360;1150 |
| 83 | H | H | —CH₂CO₂CH₂CH₃ | CNH₂ | H | H | H | 160 | 1760;1350;1155 |
| 84 | H | H | —CH₂CH₃ | CNH₂ | H | H | H | 175–80 | 1360;1155(HCl) |
| 85 | H | H | —CH₂CH₃ | CNHCOH₃ | H | H | H | 210–2 | 1680;1350;1155 |

TABLE 4

| Example no | ¹H NMR (DMSO-d₆) δ |
|---|---|
| 59 | 1,05(t,3H); 3,13(quint.,2H); 7,36(dd,1H); 8,11(dd,1H); 8,36(t,1H); 8,50(dd,1H); 10,21(b,1H) |
| 60 | 0,80(t,3H); 1,36(m,4H); 3,06(q,2H); 7,28(dd,1H); 8,01(dd,1H); 8,26(t,1H); 8,42(dd,1H); 12,03(b,1H) |
| 61 | 0,81(t,3H); 1,36(m,4H); 3,06(t,2H); 7,78(b,1H); 8,27(b,1H); 8,60(b,2H); 9,12(b,1H) |
| 62 | 1,14(t,3H); 1,40(t,3H); 3,23(q,2H); 4,58(q,2H); 7,37(m,2H); 7,76(m,2H); 8,61(s,1H) |
| 63 | 1,20(t,6H); 1,40(t,3H); 3,48(q,4H); 4,56(q,2H); 7,39(m,2H); 7,74(m,2H) |
| 64 | 1,18(t,3H); 3,04(s,3H); 3,43(q,2H); 4,03(s,3H); 7,38(m,2H); 7,70(m,2H) |
| 65 | 1,09(t,3H); 3,14(q,2H); 6,25(s,2H); 7,68(m,7H); 5,10(m,3H) |
| 66 | 1,09(t,3H); 2,26(s,3H); 3,08(q,2H); 5,53(s,2H); 7,60(m,4H); 8,49(b,1H) |
| 67 | 1,10(t,3H); 3,16(q,2H); 6,40(s,2H); 7,40(m,2H); 7,80(m,3H); 8,03(m,2H); 8,61(b,1H); 8,87(d,1H) |
| 68 | 1,10(d,3H); 1,14(t,6H); 1,37(t,3H); 1,51(m,4H); 3,02(m,6H); 3,45(m,1H); 4,58(q,2H); 7,43(dd,1H); 7,79(d,1H); 7,84(d,1H); 8,20(b,1H) |
| 69 | 1,10(d,3H); 1,14(t,6H); 1,37(t,3H); 1,51(m,4H); 3,02(m,6H); 3,45(m,1H); 4,58(q,2H); 7,33(dd,1H); 7,87(d,1H); 7,92(d,1H); 8,03(b,1H); |
| 70 | 1,17(t,3H); 1,41(t,3H); 3,24(q,2H); 4,65(q,2H); 7,58(t,1H); 8,12(d,1H); 8,19(d,1H); 8,85(s,1H) |
| 71 | 1,22(t,6H); 1,44(t,3H); 3,50(q,4H); 4,69(q,2H); 7,92(d,1H); 8,14(d,1H); 8,74(s,1H) |
| 72 | 1,22(t,6H); 1,42(t,3H); 3,49(q,4H); 4,62(q,2H); 7,98(d,1H); 8,28(d,1H); 8,61(s,1H) |
| 73 | 1,03(t,6H); 1,35(m,4H); 1,49(d,3H); 1,52(t,6H); 2,53(m,6H); 3,55(q,2H); 4,04(m,1H); 4,71(q,2H); 7,55(dd,1H); 7,89(d,1H); 7,94(d,1H) |
| 74 | 1,03(t,6H); 1,35(m,4H); 1,49(d,3H); 1,52(t,6H); 2,53(m,6H); 3,55(q,2H); 4,04(m,1H); 4,71(q,2H); 7,45(dd,1H); 7,98(d,1H); 8,03(d,1H) |
| 75 | 1,25(t,6H); 1,43(t,3H); 3,51(q,4H); 4,65(q,2H); 7,69(t,1H); 8,17(t,1H); 8,24(d,1H) |
| 76 | 1,25(t,6H); 1,32(t,3H); 3,52(q,4H); 4,62(q,2H); 7,54(t,1H); 8,13(dd,1H); 8,21(dd,1H) |
| 77 | 1,46(t,6H); 4,43(q,2H); 4,74(q,2H); 8,11(d,1H); 8,35(dd,1H); 8,71(d,1H) |
| 78 | 1,47(t,3H); 1,48(t,3H); 4,43(q,2H); 4,81(q,2H); 8,04(d,1H); 8,24(dd,1H); 8,90(d,1H) |
| 79 | 1,13(t,3H); 1,41(t,3H); 3,21(q,2H); 4,66(q,2H); 8,05(d,1H); 8,25(dd,1h); 8,64(d,1H); 8,91(b,1H) |
| 80 | 1,13(t,3H); 1,42(t,3H); 3,24(q,2H); 4,70(q,2H); 7,97(d,1H); 8,19(dd,1H); 8,79(d,1H); 8,90(b,1H) |
| 81 | 5,07(b,2H); 6,60(m,3H); 3,30(m,2H); 7,80(b,1H) |
| 82 | 5,31(b,2H); 6,41(d,1H); 6,85(m,3H); 8,15(b,2H) |
| 83 | 1,08(t,3H); 3,45(b,1H); 3,94(s,2H); 3,98(q,2H); 5,46(b,2H); 6,44(d,1H); 6,74(d,1H); 7,03(t,1H) |
| 84 | 1,09(t,3H); 3,13(q,2H; 5,35(b,2H); 6,48(d,1H); 6,86(d,1H); 7,07(t,1H); 8,04(b,1H); 12,90(b,1H) |
| 85 | 1,10(t,3H); 2,16(s,3H); 3,10(quint.,2H); 7,26(t,1H); 7,30(d,1H); 7,89(d,1H); 8,24(t,1H); 9,81(s,1H); 13,39(b,1H) |

EXAMPLES 2 TO 61

The compounds identified by Examples 2 to 61 in Tables 1, 2, 3 and 4 are prepared by the same method of preparation as described in Example 1.

EXAMPLE 86

Method B

Preparation of 3,4-dihydro-2H-2-ethyl-[1,2,5]-thiadiazino[5,6-a]benzimidazole 1,1-dioxide 4 g of tetrabutylammonium bisulfate, 45 g (0.24 mol) of 1,2-dibromoethane and 138 g (1 mol) of finely powdered potassium carbonate are added to a solution of 45 g (0.2 mol) of N-ethyl-1H-benzimidazole-2-sulfonamide in 400 ml of dimethyl sulfoxide. The mixture is stirred for 12 hours at room temperature and poured into a water/ice mixture. The precipitate obtained is filtered off and washed with water to give 44.5 g (88%) of 3,4-dihydro-2H-2-ethyl-[1,2,5]-thiadiazino[5,6-a]benzimidazole 1,1-dioxide melting at 176°–8° C.

The data for identifying the product are given in Tables 5 and 6.

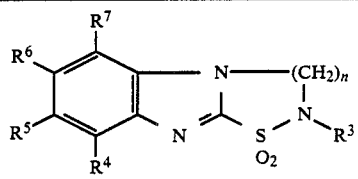

| Example no | $R^3$ | n | $R^4$ | $R^5$ | $R^6$ | $R^7$ | M.p. (°C.) | IR (KBr) |
|---|---|---|---|---|---|---|---|---|
| 86 | —CH$_2$—CH$_3$ | 2 | H | H | H | H | 176–8 | 1345;1160 |
| 87 | H | 2 | H | H | H | H | 227–30 | 1335;1170 |
| 88 | —CH$_3$ | 2 | H | H | H | H | 247–8 | 1345;1160 |
| 89 | —CH$_3$ | 3 | H | H | H | H | 177–9 | 1350;1160 |
| 90 | —CH$_2$—CH$_3$ | 3 | H | H | H | H | 120–1 | 1360;1160 |
| 91 | —CH$_2$—CH$_3$ | 4 | H | H | H | H | 155–7 | 1355;1155 |
| 92 | —(CH$_2$)$_3$—N(morpholino) | 2 | H | H | H | H | 188–90 | 1345;1165 |
| 93 | —(CH$_2$)$_2$—N(morpholino) | 3 | H | H | H | H | 132–7 | 1345;1165 |
| 94 | —CH$_2$—CH$_3$ | 2 | H | C$_6$H$_5$O— | H | H | 199–205 | 1345;1165 |
| 95 | —CH$_2$—CH$_3$ | 2 | H | H | C$_6$H$_5$O— | H | | |
| 96 | —CH$_2$—CH$_3$ | 2 | H | Cl | H | H | 156–163 | 1360;1165 |
| 97 | —CH$_2$—CH$_3$ | 2 | H | H | Cl | H | | |
| 98 | H | 3 | H | H | H | H | 251–6 | 1360;1160 |
| 99 | —CH$_2$CH$_2$—(3,4-dimethoxyphenyl) | 3 | H | H | H | H | 175–7 | 1345;1165 |
| 100 | —CH$_2$CH$_2$CH$_2$CH$_3$ | 2 | H | H | H | H | 181–3 | 1345;1170 |
| 101 | —CH$_2$CH$_3$ | 2 | Cl | CH$_3$ | CH$_3$ | Cl | 206–10 | 1350;1150 |
| 102 | —CH(CH$_3$)(CH$_2$)$_3$N(CH$_2$CH$_3$)$_2$ | 2 | H | Cl | H | H | 119–21 | 1330;1165 |
| 103 | —CH(CH$_3$)(CH$_2$)$_3$N(CH$_2$CH$_3$)$_2$ | 2 | H | H | Cl | H | 105–2 | 1320;1180 |
| 104 | —(4-chlorophenyl) | 2 | H | H | H | H | 215–23 | 1330;1170 |
| 105 | —(5-methylisoxazol-3-yl) | 2 | H | H | H | H | 203–5 | 1370;1180 |

-continued

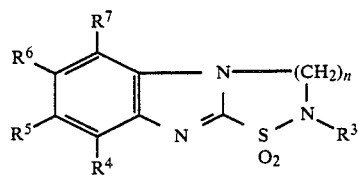

| Example no | R³ | n | R⁴ | R⁵ | R⁶ | R⁷ | M.p. (°C.) | IR (KBr) |
|---|---|---|---|---|---|---|---|---|
| 106 | -CH(CH₃)(CH₂)₃N(CH₂CH₃)₂ | 2 | H | H | H | H | 110-2 | 1320;1170 |
| 107 | -CH₂CH₃ | 2 | NO₂ | H | H | H | 218-20 | 1525;1335;1160 |
| 108 | -CH₂CH₃ | 2 | H | H | H | NO₂ | 184-5 | 1525;1355;1160 |
| 109 | -CH₂-CH₃ | 1 | H | H | H | H | 110-6 | 1330;1170 |
| 110 | Cyclohexyl | 2 | H | H | H | H | 222-3 | 1320;1175 |
| 111 | 1-Naphthyl | 2 | H | H | H | H | 274-5 | 1370;1180 |
| 112 | -CH₂CH₃ | 2 | H | CF₃ | H | H | 160-95 | 1350;1160 |
| 113 | -CH₂CH₃ | 2 | H | H | CF₃ | H | | |
| 114 | 1-Adamantyl | 2 | H | H | H | H | 300 | 1345;1170 |
| 115 | -CH₂CH₃ | 2 | H | C₆H₅-C(=O)- | H | H | 180-230 | 1660;1650;1355;1160 |
| 116 | -CH₂CH₃ | 2 | H | H | C₆H₅-C(=O)- | H | | |
| 117 | -CH₂-C₆H₄-OCH₃ | 2 | H | H | H | H | 227-30 | 1355;1165 |
| 118 | -CH₂-(2-pyridyl) | 2 | H | H | H | H | 168-70 | 1345;1165 |
| 119 | -CH₂CH₂-(2-pyridyl) | 2 | H | H | H | H | 182-4 | 1340;1165 |
| 120 | Cyclohexyl | 2 | H | Cl | H | H | 242-4 | 1325;1165 |
| 121 | Cyclohexyl | 2 | H | H | Cl | H | 267-9 | 1315;1170 |
| 122 | -CH₂CH₂N(CH₂CH₃)₂ | 2 | H | H | H | H | 163-5 | 1330;1155 |
| 123 | H | 2 | H | Cl | H | H | 255-9 | 1360;1175 |
| 124 | H | 2 | H | H | Cl | H | 258-62 | 1350;1170 |
| 125 | H | 2 | H | Cl | Cl | H | 273-6 | 1350;1175 |
| 126 | -CH₂CH₂CH₂CH₃ | 2 | NO₂ | Cl | Cl | H | 215-7 | 1550;1355;1175;1165 |
| 127 | -CH₂CH₃ | 2 | H | H | NO₂ | H | 255-8 | 1520;1350;1155 |
| 128 | -CH₂CH₃ | 2 | H | NO₂ | H | H | 208-10 | 1525;1345;1165 |
| 129 | -CH₃ | 2 | H | NO₂ | H | H | 241-5 | 1520;1350;1340;1165 |
| 130 | -CH₃ | 2 | H | H | NO₂ | H | 257-65 | 1520;1345;1165 |
| 131 | -CH₂CH₃ | 3 | H | H | NO₂ | H | 238-45 | 1520;1365;1350;1160 |
| 132 | -CH₂CH₃ | 3 | H | NO₂ | H | H | 203-8 | 1520;1355;1160 |
| 133 | -CH₂CH₂CH₂CH₃ | 2 | H | NO₂ | H | H | 165-73 | 1525;1350;1170 |
| 134 | -CH₂CH₂CH₂CH₃ | 2 | H | H | NO₂ | H | 195-7 | 1525;1350;1170 |
| 135 | -CH₂CH₂-(2-pyridyl) | 2 | H | NO₂ | H | H | 175-92 | 1525;1365;1345;1170 |

-continued

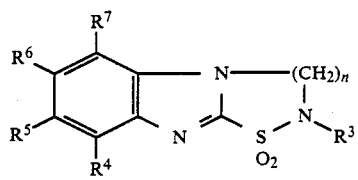

| Example no | R³ | n | R⁴ | R⁵ | R⁶ | R⁷ | M.p. (°C.) | IR (KBr) |
|---|---|---|---|---|---|---|---|---|
| 136 | —CH₂CH₂-(2-pyridyl) | 2 | H | H | NO₂ | H | | |
| 137 | —CH₂-(2-pyridyl) | 2 | H | NO₂ | H | H | 175–95 | 1525;1365;1345;1175 |
| 138 | —CH₂-(2-pyridyl) | 2 | H | H | NO₂ | H | | |
| 139 | —CH₂CH₃ | 4 | H | NO₂ | H | H | 207–10 | 1525;1350;1160 |
| 140 | —CH₂CH₃ | 4 | H | H | NO₂ | H | 240–7 | 1525;1350;1160 |
| 141 | —(CH₂)₃—N(morpholino) | 2 | H | NO₂ | H | H | 170–190 | 1525;1365;1345;1170 |
| 142 | —(CH₂)₃—N(morpholino) | 2 | H | H | NO₂ | H | | |
| 143 | —CH(CH₃)(CH₂)₃N(CH₂CH₃)₂ | 2 | H | NO₂ | H | H | 130–7 | 1530;1350;1165 |
| 144 | —CH(CH₃)(CH₂)₃N(CH₂CH₃)₂ | 2 | H | H | NO₂ | H | 145–7 | 1530;1350;1325;1170 |
| 145 | H | 2 | H | NO₂ | H | H | 240–5 | 1525;1345;1170 |
| 146 | H | 2 | H | H | NO₂ | H | 251(d) | 1525;1345;1170 |
| 147 | 1-Adamantyl | 2 | H | NO₂ | H | H | | |
| 148 | 1-Adamantyl | 2 | H | H | NO₂ | H | 217–23 | 1530;1350;1170 |
| 149 | —CH₂CH₃ | 2 | H | H | NH₂ | H | 232–4 | 3430;3330;1355;1155 |
| 150 | —CH₂CH₃ | 2 | H | H | CH₃C(O)NH— | H | 245–8 | 1690;1350;1155 |
| 151 | —CH₂CH₃ | 2 | H | H | —NCS | H | 218–25 | 2100;1350;1160 |
| 152 | —CH₂CO₂CH₂CH₃ | 2 | H | Cl | H | H | 192–4 | 1755;1340;1170 |
| 153 | —CH₂CO₂CH₂CH₃ | 2 | H | H | Cl | H | 163–5 | 1745;1350;1170 |
| 154 | —(CH₂)₆—Cl | 2 | H | Cl | H | H | 154–7 | 1345;1170 |
| 155 | —(CH₂)₆—Cl | 2 | H | H | Cl | H | 167–8 | 1350;1170 |
| 156 | —CH₂CH₂Cl | 2 | H | Cl | H | H | 216 | 1350;1170 |
| 157 | —CH₂CH₂Cl | 2 | H | H | Cl | H | 218–20 | 1345;1165 |
| 158 | —CH₂CH₂CH₂Cl | 2 | H | H | NO₂ | H | 210–4 | 1345;1170 |
| 159 | —(CH₂)₄—CN | 2 | H | Cl | H | H | 179–80 | 2240;1340;1160 |
| 160 | —(CH₂)₄—CN | 2 | H | H | Cl | H | 192–6 | 2240;1355;1165 |

-continued

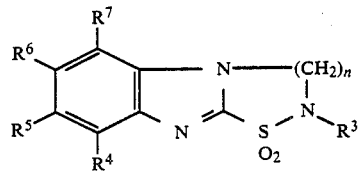

| Example no | R³ | n | R⁴ | R⁵ | R⁶ | R⁷ | M.p. (°C.) | IR (KBr) |
|---|---|---|---|---|---|---|---|---|
| 161 | $-(CH_2)_3-N(CH_3)-(CH_2)_2$-(3,4-dimethoxyphenyl) | 2 | H | H | $NO_2$ | H | 104–9 | 1520;1350;1335;1165 |
| 162 | $-(CH_2)_6-N(CH_2CH_3)_2$ | 2 | H | Cl | H | H | 125–32 (HCl) | 1370;1180(HCl) |
| 163 | $-(CH_2)_6-N(CH_2CH_3)_2$ | 2 | H | H | Cl | H | 128–38 (HCl) | 1355;1175(HCl) |
| 164 | $-CH_2-CN$ | 2 | H | Cl | H | H | 185–7 | 2225;1370;1180 |
| 165 | $-CH_2-CN$ | 2 | H | H | Cl | H | 243–5 | 225,1370,1180, |
| 166 | $-CH_2CH_2N(CH_2CH_3)_2$ | 2 | H | Cl | H | H | 212–3 | 1335;1160 |
| 167 | $-CH_2CH_2N(CH_2CH_3)_2$ | 2 | H | H | Cl | H | 193–6 | 1340;1165 |
| 168 | $-(CH_2)_6-NHCH_2CH_3$ | 2 | H | H | Cl | H | 241–3 (HCl) | 1335;1165(HCl) |
| 169 | 2-pyridylmethyl | 2 | H | H | Cl | H | 205–9 | 1370;1170 |

TABLE 6

| Example n° | ¹H NMR (DMSO-d₆) δ |
|---|---|
| 86 | 1,30(t,3H); 3,36(q,2H); 4,20(t,2H); 4,45(t,2H); 7,34–7,90(m,4H) |
| 87 | 3,95(t,2H); 4,34(t,2H); 7,36–7,85(m,4H); 8,28(b,1H) |
| 88 | 2,99(s,3H); 4,17(t,2H); 4,48(t,2H); 7,35–7,88(m,4H) |
| 89 | 2,03(quint.,2H); 2,72(s,3H); 3,79(t,2H); 4,63(t,2H); 7,43(m,2H); 7,80(m,2H) |
| 90 | 1,06(t,3H); 1,93(quint.,2H); 2,96(q,2H); 3,73(t,2H); 4,59(t,2H); 7,38(m,2H); 7,75(m,2H) |
| 91 | 1,14(t,3H); 1,30(m,2H); 1,99(quint.,2H); 3,09(q,2H); 3,59(t,2H); 4,85(t,2H); 7,40(m,2H); 7,77(m,2H) |
| 92 | 1,95(quint.,2H); 2,52(m,6H); 3,49(t,2H); 3,71(m,4H); 4,33(t,2H); 4,57(t,2H); 7,48–8,05(m,4H) |
| 93 | 2,05(cuint.,2H); 2,25(t,4H); 2,48(t,2H); 3,22(t,2H); 3,34(t,4H); 3,84(t,2H); 4,65(t,2H); 7,43(m,2H); 7,80(m,2H) |
| 94 | 1,25(t,3H); 3,35(q,2H); 4,24(t,2H); 4,51(t,2H); 6,91(m,2H); 7,35(m,5H); 7,70(d,1H) |
| 95 | 1,27(t,3H); 3,38(q,2H); 4,24(t,2H); 4,51(t,2H); 6,89(m,2H); 7,36(m,5H); 7,74(d,1H) |
| 96 | 1,24(t,3H); 3,36(q,2H); 4,19(t,2H); 4,45(t,2H); 7,5(dd,1H); 7,72(d,1H); 7,90(d,1H) |
| 97 | 1,24(t,3H); 3,36(q,2H); 4,18(t,2H); 4,43(t,2H); 7,40(dd,1H); 7,81(d,1H); 7,82(d,1H) |
| 98 | 1,96(quint.,2H); 2,94(t,1H); 3,75(m,2H); 4,60(m,2H); 7,38(m,2H); 7,78(m,2H) |
| 99 | 2,90(t,2H); 3,53(t,2H); 3,72(s,6H); 4,16(t,2H); 4,43(t,2H); 6,85(m,3H); 7,35–7,88(m,4H) |
| 100 | 0,93(t,3H); 1,52(m,4H); 3,32(t,2H); 4,19(t,2H); 4,46(t,2H); 7,38–7,86(m,4H) |
| 101 | 1,28(t,3H); 2,40(s,6H); 3,35(q,2H); 4,14(t,2H); 4,77(t,2H) |
| 102 | 0,91(t,6H); 1,23(d,3H); 1,43(m,4H); 2,40(m,6H); 3,69(m,1H); 4,14(t,2H); 4,38(t,2H); 7,50(dd,1H); 7,74(d,1H); 7,90(d,1H) |
| 103 | 0,86(t,6H); 1,19(d,3H); 1,39(m,4H); 2,34(m,6H); 3,42(m,1H); 4,10(t,2H); 4,34(t,2H); 7,39(dd,1H); 7,81(d,1H); 7,83 (d,1H) |
| 104 | 4,57(m,4H); 7,30–7,98(m,8H) |
| 105 | 2,38(s,H); 4,69(m,4H); 6,42(s,1H); 7,55(m,4H) |
| 106 | 0,89(t,6H); 1,23(d,3H); 1,47(m,4H); 2,37(m,6H); 3,40(m,1H); 4,14(t,2H); 4,33(t,2H); 7,39–7,87(m,4H) |
| 107 | 1,28(t,3H); 3,41(q,2H); 4,25(t,2H); 4,56(t,2H); 7,66(t,1H); 8,15(d,1H); 8,23(d,1H) |
| 108 | 1,28(t,3H); 3,43(q,2H); 4,15(t,2); 4,57(t,2H); 7,56(t,1H); 8,16(d,1H); 8,24(d,1H) |
| 109 | 1,20(t,3H); 3,32(q,2H); 6,13(s,2H); 7,40–7,87(m,4H) |
| 110 | 1,00–1,76(m,10H); 3,86(m,1H); 4,17(t,2H); 4,36(t,2H); 7,30–7,85(m,4H) |
| 111 | 4,63(m,4H); 7,40–8,35(m,11H) |
| 112 | 1,27(t,3H); 3,41(q,2H); 4,23(t,2H); 4,52(t,2H); 7,80(d,1H); 7,99(d,1H); 8,14(s,1H) |
| 113 | 1,27(t,3H); 3,41(q,2H); 4,23(t,2H); 4,52(t,2H); 7,66(d,1H); 7,80(d,1H); 8,15(s,1H) |
| 114 | 1,54(m,6H); 1,65(m,6H); 2,14(m,3H); 4,22(t,2H); 4,34(t,2H); 7,36(m,3H); 7,89(m,1H) [CDCl₃] |
| 115 | 1,26(t,3H); 3,39(q,2H); 4,21(t,2H); 4,53(t,2H); 7,51–7,87(m,7H); 8,03(d,1H) |
| 116 | 1,26(t,3H); 3,39(q,2H); 4,21(t,2H); 4,53(t,2); 7,50–7,92(m,7H); 8,09(d,1H) |
| 117 | 3,77(s,3H); 4,05(t,2H); 4,40(t,2H); 4,48(s,2H); 6,93(d,2H); 7,36(d,2H); 7,47(m,4H) |
| 118 | 4,23(t,2H); 4,47(t,2H); 4,63(s,2H); 7,20–7,95(m,7H); 8,48(ddd,1H) |
| 119 | 3,17(t,2H); 3,78(t,2H); 4,22(t,2H); 4,47(,2H); 7,13–7,86(,7H); 8,49(ddd,1H) |
| 120 | 1,25(m,2H); 1,68(m,8H); 3,84(m,1H); 4,16(t,2H); 4,36(t,2H); 7,46(dd,1H); 7,67(d,1H); 7,84(d,1H) |
| 121 | 1,24(m,2H); 1,67(m,8H); 3,84(m,1H); 4,16(t,2H); 4,36(t,2H); 7,39(dd,1H); 7,77(d,1H); 7,80(d,1H) |
| 122 | 0,95(t,6H); 2,50(q,4H); 2,69(t,2H); 3,40(t,2H); 4,27(t,2H); 4,48(t,2H); 7,30–7,87(m,4H) |
| 123 | 3,96(t,2H); 4,35(t,2H); 7,47(dd,1H); 7,71(d,1H); 7,88(d,1H); 8,35(b,1H) |
| 124 | 3,94(t,2H); 4,33(t,2H); 7,40(dd,1H); 7,82(d,1H); 7,83(d,1H); 8,26(b,1H) |
| 125 | 3,93(t,2H); 4,33(t,2H); 8,12(s,1H); 8,14(s,1H); 8,42(b,1H) |

TABLE 6-continued

| Example n° | $^1$H NMR (DMSO-$d_6$) δ |
|---|---|
| 126 | 0,90(t,3H); 1,30(m,2H); 1,58(m,2H); 3,32(t,2H); 4,20(t,2H); 4,49(t,2H); 8,51(s,1H) |
| 127 | 1,25(t,3H); 3,38(q,2H); 4,23(t,2H); 4,58(t,2H); 8,02(d,1H); 8,25(dd,1H); 8,74(d,1H) |
| 128 | 1,27(t,3H); 3,40(q,2H); 4,23(t,2H); 4,54(t,2H); 7,88(d,1H); 8,31(dd,1H); 8,67(d,1H) |
| 129 | 3,03(s,3H); 4,21(t,2H); 4,58(t,2H); 7,88(d,1H); 8,31(dd,1H); 8,66(d,1H) |
| 130 | 3,02(s,3H); 4,22(t,2H); 4,64(t,2H); 8,00(dd,1H); 8,24(dd,1H); 3,68(d,1H) |
| 131 | 1,10(t,3H); 2,00(quint.,2H); 3,04(q,2H); 3,79(t,2H); 4,77(t,2H); 8,00(d,1H); 8,21(dd,1H); 8,88(d,1H) |
| 132 | 1,11(t,3H); 2,04(quint.,2H); 3,10(q,2H); 3,79(t,2H); 4,71(t,2H); 7,94(d,1H); 8,27(dd,1H); 8,63(d,1H) |
| 133 | 0,93(t,3H); 1,51(m,4H); 3,36(t,2H); 4,23(t,2H); 4,55(t,2H); 7,87(d,1H); 8,29(dd,1H); 8,64(d,1H) |
| 134 | 0,93(t,3H); 1,51(m,4H); 3,36(t,2H); 4,24(t,2H); 4,61(t,2H); 8,07(d,1H); 8,20(dd,1H); 8,65(d,1H) |
| 135 | 3,18(t,2H); 3,82(t,2H); 4,27(t,2H); 4,57(t,2H); 7,24(m,2H); 7,67(m,1H); 7,85(d,1H); 8,29(dd,1H); 8,46(d,1H); 8,63(d,1H) |
| 136 | 3,18(t,2H); 3,82(t,2H); 4,27(t,2H); 4,63(t,2H); 7,24(m,2H); 7,69(m,1H); 8,00(d,1H); 8,21(dd,1H); 8,46(d,1H); 8,65(d,1H) |
| 137 | 4,28(t,2H); 4,53(t,2H); 4,73(s,2H); 7,28(m,1H); 7,49(m,1H); 7,78(m,1H); 7,86(d,1H); 8,31(dd,1H); 8,38(m,1H); 8,65(d,1H) |
| 138 | 4,28(t,2H); 4,54(t,2H); 4,73(s,2H); 7,28(m,1H); 7,49(m,1H); 7,78(m,1H); 7,96(d,1H); 8,23(dd,1H); 8,38(m,1H); 8,70(d,1H) |
| 139 | 1,15(t,3H); 1,40(m,2H); 2,06(quint.,2H); 3,13(q,2H); 3,65(t,2H); 4,91(t,2H); 8,01(d,1H); 8,31(dd,1H); 8,7(d,1H) |
| 140 | 1,15(t,3H); 1,40(m,2H); 2,04(quint.,2H); 3,14(q,2H); 3,62(t,2H); 4,97(t,2H); 8,01(d,1H); 8,22(dd,1H); 8,83(d,1H) |
| 141 | 2,02(quint,2H); 3,04(m,6H); 3,43(t,2H); 3,78(m,4H); 4,25(t,2H); 4,56(t,2H); 7,92(d,1H); 8,34(dd,1H); 8,69(d,1H) |
| 142 | 2,02(quint,2H); 3,04(m,6H); 3,43(t,2H); 3,78(m,4H); 4,25(t,2H); 4,62(t,2H); 8,01(d,1H); 8,25(dd,1H); 8,71(d,1H) |
| 143 | 0,90(t,6H); 1,23(d,3H); 1,48(m,4H); 2,40(q,6H); 3,43(m,1H); 4,16(m,2H); 4,46(t,2H); 7,89(d,1H); 8,32(dd,1H); 8,69(d,1H) |
| 144 | 0,90(t,6H); 1,24(d,3H); 1,45(m,4H); 2,39(q,6H); 3,43(m,1H); 4,17(m,2H); 4,53(t,2H); 8,02(d,1H); 8,27(dd,1H); 8,73(d,1H) |
| 145 | 4,00(t,2H); 4,44(t,2H); 7,88(d,1H); 8,30(d,1H); 8,47(b,1H); 8,67(d,1H) |
| 146 | 4,01(t,2H); 4,51(t,2H); 8,01(d,1H); 8,26(dd,1H); 8,48(b,1H); 8,71(d,1H) |
| 147 | 1,57(b,12H); 2,03(b,3H); 3,95(t,2H); 4,43(t,2H); 7,90(d,1H); 8,33(dd,1H); 8,73(d,1H) |
| 148 | 1,57(b,12H); 2,03(b,3H); 4,01(t,2H); 4,49(t,2H); 8,00(d,1H); 8,24(dd,1H); 8,69(d,1H) |
| 149 | 1,22(t,3H); 3,29(q,2H); 4,16(m,4H); 5,36(b,2H); 6,58(d,1H); 6,75(dd,1H); 7,45(d,1H) |
| 150 | 1,24(t,3H); 2,10(s,3H); 3,34(q,2H); 4,16(t,2H); 4,36(t,2H); 7,37(d,1H); 7,70(d,1H); 8,10(s,1H); 10,06(s,1H) |
| 151 | 1,25(t,3H); 3,36(q,2H); 4,19(t,2H); 4,41(t,2I); 7,39(dd,1H); 7,84(d,1H; J = 2 Hz); 7,84(d,1H, J = 8,6 Hz) |
| 152 | 1,10(t,3H); 4,07(q,2H); 4,30(m,4H); 4,34(s,2H); 7,49(dd,1H); 7,74(d,1H); 7,89(d,1H) |
| 153 | 1,11(t,3H); 4,08(q,2H); 4,31(m,4H); 4,33(s,2H); 7,41(dd,1H); 7,82(d,1H); 7,86(d,1H) |
| 154 | 1,53(m,8H); 3,30(t,2H); 3,61(t,2H); 4,18(t,2H); 4,45(t,2H); 7,47(dd,1H); 7,71(d,1H); 7,87(d,1H) |
| 155 | 1,55(m,8H); 3,30(t,2H); 3,61(t,2H); 4,18(t,2H); 4,43(t,2H); 7,39(d,1H); 7,79(d,1H); 7,83(d,1H) |
| 156 | 3,69(t,2H); 3,87(t,2H); 4,26(t,2H); 4,47(t,2H); 7,48(dd,1H); 7,73(d,1H); 7,89(d,1H) |
| 157 | 3,69(t,2H); 3,88(t,2H); 4,27(t,2H); 4,46(t,2H); 7,40(dd,1H); 7,82(d,1H); 7,86(d,1H) |
| 158 | 2,14(quint., 2H); 3,51(t,2H); 3.73(t,2H); 4,25(t,2H); 4,62(t,2H); 8,00(d,1H); 8,24(dd,1H); 8,71(d,1H) |
| 159 | 1,68(m,4H); 2,54(t,2H); 3,36(t,2H); 4,18(t,2H); 4,45(t,2H); 7,49(dd,1H); 7,73(d,1H); 7,90(d,1H) |
| 160 | 1,70(m,4H); 2,54(t,2H); 3,34(t,2H); 4,19(t,2H); 4,44(t,2H); 7,39(d,1H); 7,81(d,1H); 7,84(d,1H) |
| 161 | 1,87(quint., 2H); 2,29(s,3H); 2,64(m,6H); 3,29(t,2H); 3,86(s,6H); 4,15(m,4H); 6,76(m,3H); 7,83(d,1H); 8,19(dd,1H); 8,33(d,1H) |
| 162 | 0,91(t,6H); 1,45(m,8H); 2,36(t,2H); 2,39(q,4H); 3,28(t,2H); 4,18(t,2H); 4,44(t,2H); 7,46(dd,1H); 7,72(d,1H); 7,86(d,1H) |
| 163 | 0,91(t,6H); 1,45(m,8H); 2,37(t,2H); 2,40(q,4H); 3,28(t,2H); 4,18(t,2H); 4,44(t,2H); 7,38(dd,1H); 7,80(d,1H); 7,83(d,1H) |
| 164 | 4,40(t,2H); 4,47(t,2H); 4,71(s,2H); 7,51(dd,1H); 7,77(d,1H); 7,92(d,1H) |
| 165 | 4,42(m,4H); 4,71(s,2H); 7,44(dd,1H); 7,82(d,1H); 7,91(d,1H) |
| 166 | 0,95(t,6H); 2,51(q,4H); 2,70(t,2H); 3,40(t,2H); 4,24(t,2H); 4,46(t,2H); 7,45(dd,1H); 7,68(d,1H); 7,84(d,1H) |
| 167 | 0,93(t,6H); 2,48(q,4H); 2,66(t,2H); 3,37(t,2H); 4,23(t,2H); 4,44(t,2H); 7,39(dd,1H); 7,80(d,1H); 7,83(d,1H) |
| 168 | 0,98(t,3H); 1,47(m,8H); 3,10(m,5H); 3,28(t,2H); 4,16(t,2H); 4,42(t,2H); 7,40(dd,1H); 7,81(d,1H); 7,83(d,1H) |
| 169 | 4,71(m,4H); 7,41(m,2H); 7,50(dd,1H); 7,84(d,1H); 7,92(m,2H); 8,38(d,1H) |

EXAMPLES 87 TO 126 AND 170 TO 176

The compounds identified by Examples 87 to 126 and 170 to 176 in Tables 5 to 10 are prepared by the same method of preparation as described in Example 86.

EXAMPLE 180

Method

Preparation of 1,2,3,4,13,14-hexahydropyrido[1',2':2,3]-[1,2,5]-thiadiazino[5,6-a]-benzimidazole 6,6-dioxide 2.95 g (0.01 mol) of 2-(sulfonyl-2-hydroxymethyl-1-piperidinyl)-1H-benzimidazole are refluxed for 1 hour in 20 ml of thionyl chloride. The mixture is evaporated to dryness and the residue is recrystallized from an ethanol/ethyl acetate mixture (1:1) to give 2.0 g (73%) of 1,2,3,4,13,14-hexahydropyrido[1',2':2,3]-[1,2,5]-thiadiazino[5,6-a]benzimidazole 6,6-dioxide melting at 246°-8° C.

The data for identifying the product are given in Tables 11 and 12.

EXAMPLE 177

Method D

Preparation of 2H-2-ethyl-3-phenyl-[1,2,5]-thiadiazino[5,6-a]benzimidazole 1,1-dioxide A mixture of 13.7 g (0.04 mol) of 1-benzoylmethyl-N-ethyl-1H-benzimidazole-2-sulfonamide and 230 g of polyphosphoric acid is stirred at 125° C. for 4 hours. The resulting solution is poured onto ice and the product is filtered off and washed with water, then with an aqueous solution of sodium bicarbonate and again with water to give 8.7 g (67%) of 2H-2-ethyl-3-phenyl-[1,2,5]-thiadiazino[5,6-a]benzimidazole 1,1-dioxide melting at 155°-8° C.

The data for identifying the product are given in Tables 9 and 10.

TABLE 7

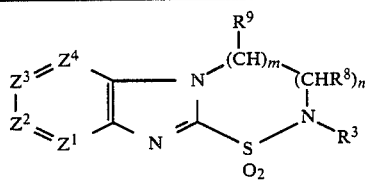

| Example no | R³ | n | m | R⁸ | R⁹ | Z¹ | Z² | Z³ | Z⁴ | M.p.(°C.) | IR (KBr) |
|---|---|---|---|---|---|---|---|---|---|---|---|
| 170 | —CH₂CH₃ | 1 | 1 | CH₃ | H | CH | CH | CH | CH | 137–41 | 1340;1180;1155 |
| 171 | —CH₂CH₃ | 1 | 1 | CH₃ | H | CH | C—NO₂ | CH | CH |  |  |
| 172 | —CH₂CH₃ | 1 | 1 | CH₃ | H | CH | CH | C—NO₂ | CH | 170–200 | 1520;1350;1180;1155 |
| 173 | —(CH₂)₃CH₃ | 1 | 1 | H | H | CH | CH | CH | N | 143–5 | 1355;1175;1160 |
| 174 | —(CH₂)₃CH₃ | 1 | 1 | H | H | CH | N | CH | CH | 227–31 | 1355;1165 |
| 175 | —CH₂CH₃ | 1 | 0 | C₆H₅ | — | CH | CH | CH | CH | 120–2 | 1320;1170 |

TABLE 8

| Example no | ¹H NMR (DMSO-d₆) δ |
|---|---|
| 170 | 1,20(t,3H); 1,49(d,3H); 3,25(q,2H); 4,37(d,2H); 4,67(m,1H); 7,31–7,85(m,4H) |
| 171 | 1,22(t,3H); 1,53(d,3H); 3,32(q,2H); 4,04–4,83(m,3H); 7,87(d,1H); 8,31(dd,1H); 8,67(d,1H) |
| 172 | 1,22(t,3H); 1,53(d,3H); 3,32(q,2H); 4,10–4,78(m,3H); 7,97(d,1H); 8,22(dd,1H); 8,72(d,1H) |
| 173 | 0,91(t,3H); 1,45(m,4H); 3,34(t,2H); 4,18(t,2H); 4,46(t,2H); 7,48(dd,1H); 8,27(dd,1H); 8,57(dd,1H) |
| 174 | 0,92(t,3H); 1,46(m,4H); 3,32(t,2H); 4,17(t,2H); 4,47(t,2H); 7,73(dd,1H); 8,52(d,1H); 9,12(dd,1H) |
| 175 | 1,18(t,3H); 3,28(q,2H); 7,01(s,1H); 6,90–7,46(m,3H); 7,55(s,5H); 7,88(m,1H) |

TABLE 9

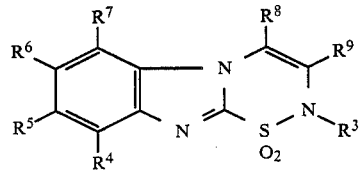

| Example no | R⁸ | R⁹ | R³ | R⁴ | R⁵ | R⁶ | R⁷ | M.p.(°C.) | IR (KBr) |
|---|---|---|---|---|---|---|---|---|---|
| 176 | H | H | —CH₂CH₃ | H | H | H | H | 123–7 | 1350;1160 |
| 177 | H | C₆H₅ | —CH₂CH₃ | H | H | H | H | 155–8 | 1365;1180 |
| 178 | H | —CH₃ | —CH₂CH₃ | H | H | H | H | 153–5 | 1355;1180 |
| 179 | H | p-NO₂-C₆H₄ | —CH₂CH₃ | H | H | NO₂ | H | 307–15 | 1520;1380;1340;1185 |

TABLE 10

| Example no | ¹H NMR (DMSO-d₆) δ |
|---|---|
| 176 | 1,26(t,3H); 3,78(q,2H); 6,76(d,1H); 7,52(m,2H); 7,73(d,1H); 7,95(m,2H) |
| 177 | 0,75(t,3H); 3,55(q,2H); 7,53(m,5H); 7,83(m,3H); 8,21(d,1H); 8,51(s,1H) |
| 178 | 1,00(t,3H); 2,20(s,3H); 3,75(q,2H); 7,47(m,2H); 7,76(s,1H); 7,90(m,2H) |
| 179 | 0,78(t,3H); 3,57(q,2H); 8,12(m,3H); 8,37(m,3H); 8,88(s,1H); 9,33(d,1H) |

TABLE 11

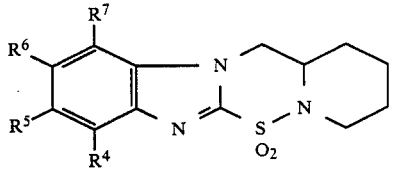

| Example no | R⁴ | R⁵ | R⁶ | R⁷ | M.p.(°C.) | IR (KBr) |
|---|---|---|---|---|---|---|
| 180 | H | H | H | H | 246–8 | 1350;1165 |
| 181 | H | NO₂ | H | H | 250–66 | 1520;1365;1350;1170 |
| 182 | H | H | NO₂ | H |  |  |

TABLE 12

| Example n° | $^1$H NMR (DMSO-$d_6$) δ |
|---|---|
| 180 | 1,82(m,6H); 3,02(m,1H); 4,39(m,2H); 4,71(d,2H); 7,31–7,88(m,4H) |
| 181 | 1,80(m,6H); 3,38(m,1H); 4,50(m,2H); 4,65(d,2H); 7,80(d,1H); 8,34(dd,1H); 8,62(d,1H) |
| 182 | 1,85(m,6H); 3,52(m,1H); 4,60(m,2H); 4,73(d,2H); 8,01(d,1H); 8,24(dd,1H); 8,67(d,1H) |

EXAMPLE 178

The compound identified by Example 178 in Tables 9 and 10 is prepared by the same method of preparation as described in Example 177.

EXAMPLE 62

Method E

Preparation of 1,N-diethyl-1H-benzimidazole-2-sulfonamide 46.8 g (0.3 mol) of ethyl iodide are added to a suspension of 67.5 g (0.3 mol) of N-ethyl-1H-benzimidazole-2-sulfonamide and 47.7 g (0.45 mol) of sodium carbonate in 450 ml of acetone and 20 ml of water. The mixture is left under reflux for 20 hours, the acetone is evaporated off, 200 ml of water are added and the product is extracted with methylene chloride. The organic layer is dried (Na$_2$SO$_4$) and evaporated. The residue is recrystallized from an ethanol/water mixture (2:1) to give 56.8 g (75%) of 1,N-diethyl-1H-benzimidazole-2-sulfonamide melting at 135°–9° C.

The data for identifying the product are given in Tables 3 and 4.

EXAMPLES 63 TO 70

The compounds identified by Examples 63 to 70 in Tables 3 and 4 are prepared by the same method of preparation as described in Example 62.

EXAMPLE 71

Method F

Preparation of 6-nitro-1,N,N-triethyl-1H-benzimidazole-2-sulfonamide 2.6 g (0.11 mol) of sodium hydride are added to a solution of 29.8 g (0.1 mol) of 6-nitro-1,N-diethyl-1H-benzimidazole-2-sulfonamide in 100 ml of dimethylformamide. The solution is stirred for one hour at 40° C., 10.8 g (0.1 mol) of ethyl bromide are added and the mixture is stirred for 12 hours at 50° C. It is poured into water and the product is filtered off and washed with water. The precipitate is recrystallized from ethanol to give 25.6 g (78%) of 6-nitro-1,N,N-triethyl-1H-benzimidazole-2-sulfonamide melting at 90°–1° C.

The data for identifying the product are given in Tables 3 and 4.

EXAMPLES 72 TO 76

The compounds identified by Examples 72 to 76 in Tables 3 and 4 are prepared by the same method of preparation as described in Example 71.

EXAMPLE 134

Method G

Preparation of 2H-2-butyl-3,4-dihydro-7-nitro-[1,2,5]-thiadiazino[5,6-a]benzimidazole 1,1-dioxide 2.6 g (0.11 mol) of sodium hydroxide are added to a solution of 26.8 g (0.1 mol) of 3,4-dihydro-2H-7-nitro-[1,2,5]-thiadiazino[5,6-a]benzimidazole 1,1-dioxide in 200 ml of dimethylformamide. The solution is stirred for one hour at room temperature and 13.6 g (0.1 mol) of butyl bromide are then added. Stirring is continued for a further 3 hours at 40° C., the mixture is poured into water and the product is filtered off and washed with water. The precipitate is recrystallized from acetonitrile to give 29.2 g (90%) of 2H-2-butyl-3,4-dihydro-7-nitro-[1,2,5]-thiadiazino[5,6-a]benzimidazole 1,1-dioxide melting at 195°–7° C.

The data for identifying the product are given in Tables 5 and 6.

EXAMPLES 86, 88 TO 97, 115 TO 122, 126 TO 138 AND 152 TO 169

The compounds identified by Examples 86, 88 to 97, 115 to 122, 126 to 138 and 152 to 169 in Tables 5 and 6 are prepared by the same method of preparation as described in Example 134.

EXAMPLES 127 AND 128

Method H

Preparation of 3,4-dihydro-2H-2-ethyl-7-nitro-[1,2,5]-thiadiazino[5,6-a]benzimidazole 1,1-dioxide and 3,4-dihydro-2H-2-ethyl-8-nitro-[1,2,5]-thiadiazino[5,6-a]benzimidazole 1,1-dioxide A cold solution (at between 5° C. and 10° C.) consisting of 45 ml of concentrated sulfuric acid and 55 ml of 65% nitric acid is added dropwise to a solution of 100.4 g (0.4 mol) of 3,4-dihydro-2H-2-ethyl-[1,2,5]-thiadiazino[5,6-a]benzimidazole 1,1-dioxide in 500 ml of concentrated sulfuric acid at 5° C. When the addition is complete, the mixture is stirred for 2 hours at room temperature and poured onto ice and the product is filtered off and washed with water and ethanol to give 110.1 g (93%) of a mixture of two isomers. Fractional recrystallization from nitromethane gives 51.3 g of 3,4-dihydro-2H-2-ethyl-7-nitro-[1,2,5]-thiadiazino[5,6-a]benzimidazole 1,1-dioxide melting at 255°–8° C. and 47.8 g of 3,4-dihydro-2H-2-ethyl-8-nitro-[1,2,5]-thiadiazino[5,6-a]benzimidazole 1,1-dioxide melting at 208°–10° C.

The data for identifying the products are given in Tables 5 and 6.

EXAMPLES 34 TO 38, 42, 71, 72, 77 TO 80, 129 TO 148, 171, 172, 179, 181 AND 182

The compounds identified by Examples 34 to 38, 42, 71, 72, 77 to 80, 129 to 148, 171, 172, 179, 181 and 182 in Tables 1 to 12 are prepared by the same method of preparation as described in Examples 127 and 128.

EXAMPLE 149

Method J

Preparation of
7-amino-3,4-dihydro-2H-2-ethyl-[1,2,5]-thiadiazino[5,6-a]benzimidazole 1,1 dioxide A solution of 5.9 g (0.02 mol) of 3,4-dihydro-2H-2-ethyl-7-nitro-[1,2,5]-thiadiazino[5,6-a]benzimidazole 1,1-dioxide in 200 ml of methanol, containing 0.2 g of 10% palladium-on-charcoal, is hydrogenated at room temperature for 12 hours at a pressure of 60 psi. The mixture is filtered and the methanol is concentrated to give 4.6 g (87%) of 7-amino-3,4-dihydro-2H-2-ethyl-[1,2,5]-thiadiazino[5,6-a]benzimidazole 1,1-dioxide melting at 232°–4° C.

The data for identifying the product are given in Tables 5 and 6.

EXAMPLES 81 TO 84

The compounds identified by Examples 81 to 84 in Tables 3 and 4 are prepared by the same method of preparation as described in Example 149.

EXAMPLE 150

Method K

Preparation of
7-acetylamino-3,4-dihydro-2H-2-ethyl-[1,2,5]-thiadiazino[5,6-a]benzimidazole 1,1-dioxide 1.6 g (0.02 mol) of acetyl chloride are added slowly to a solution of 5.3 g (0.02 mol) of 7-amino-3,4-dihydro-2H-2-ethyl-[1,2,5]-thiadiazino[5,6-a]benzimidazole 1,1-dioxide in 25 ml of pyridine cooled in a water/ice bath. When the addition is complete, the mixture is stirred for 2 hours at room temperature and poured onto ice. The product is filtered off, washed with water and dried to give 4.2 g (68%) of 7-acetylamino-3,4-dihydro-2H-2-ethyl-[1,2,5]-thiadiazino[5,6-a]benzimidazole 1,1-dioxide melting at 245°–8° C.

The data for identifying the product are given in Tables 5 and 6.

EXAMPLES 44, 45 AND 85

The compounds identified by Examples 44, 45 and 85 in Tables 1, 2, 3 and 4 are prepared by the same method of preparation as described in Example 150.

EXAMPLE 151

Method L

Preparation of
3,4-dihydro-2H-2-ethyl-7-isothiocyanato-[1,2,5]-thiadiazino[5,6-a]benzimidazole 1,1-dioxide A solution of 4.5 g (0.017 mol) of 7-amino-3,4-dihydro-2H-2-ethyl-[1,2,5]-thiadiazino[5,6-a]benzimidazole 1,1-dioxide in 100 ml of 4N hydrochloric acid is added, with stirring, to a solution of 2 ml (0.02 mol) of thiophosgene in 100 ml of chloroform. The mixture is stirred at room temperature until the orange color of the organic layer has disappeared (about 6 hours), and the latter is separated off by decantation, washed with water, dried over sodium sulfate and evaporated to dryness. The residue is recrystallized from an acetone/water mixture (9:1) to give 3.0 g (49%) of 3,4-dihydro-2H-2-ethyl-7-isothiocyanato-[1,2,5]-thiadiazino[5,6-a]benzimidazole 1,1-dioxide melting at 218°–25° C.

The data for identifying the product are given in Tables 5 and 6.

EXAMPLE 103

Method M

Preparation of
7-chloro-3,4-dihydro-2H-2-(4-diethylamino-1-methylbutyl)-[1,2,5]-thiadiazino[5,6-a]benzimidazole 1,1-dioxide A solution of 1.5 g (0.022 mol) of sodium nitrite in 5 ml of water is added dropwise to a solution of 7.58 g (0.02 mol) of 7-amino-3,4-dihydro-2H-2-(4-diethylamino-1-methylbutyl)-[1,2,5]-thiadiazino[5,6-a]benzimidazole 1,1-dioxide in 50 ml of 12N hydrochloric acid, the temperature being kept between −5° C. and 0° C. When the addition is complete, the mixture is stirred for 15 minutes at the same temperature and the whole of it is poured into a solution of 4.4 g (0.044 mol) of cuprous chloride in 25 ml of concentrated hydrochloric acid, cooled to 0° C. beforehand, the mixture being added in several portions over a period of 5 minutes, taking care to avoid excessive effervescence. When the addition is complete, the mixture is left to warm up to room temperature, with continued stirring, and then heated to a temperature of 70° C. It is left to cool to room temperature and 100 ml of water are added. The product is filtered off, washed with water and dried to give 2.5 g (31%) of 7-chloro-3,4-dihydro-2H-2-(4-diethylamino-1-methylbutyl)-[1,2,5]-thiadiazino[5,6-a]benzimidazole 1,1-dioxide melting at 150°–2° C.

The data for identifying the product are given in Tables 5 and 6.

Inhibitory activity on gastric acid secretion, Shay's method

[H. Shay; S. A. Komarov; S. S. Fels; D. Merange; M. Grvenstein; H. Siplet: Gastroenterology, 5, 43 (1945)—F. E. Visscher; P. H. Seay; A. P. Taxelaar; W. Veldkamp; M. J. Vander Brook; J. Pharmac. Exp. Ther., 110, 188 (1954)—"Animal Experiments in Pharmacological Analysis", F. R. Domer; C. C. Thomas, published by Springfield, Ill., USA, 1970, p. 140].

Male Wistar rats weighing 200 to 250 grams are used in this test; they are tested from the day preceding the day of the test, with free access to water. Groups containing a minimum of 4 animals each are used.

The rats are anesthetized with ethyl ether, a laparotomy is performed on them and their pylorus is ligated; the abdominal incision is then sewn up. The administration of the products, with the vehicle for the control group, is effected intraduodenally (i.d.) before the abdominal incision is sewn up. The dose administered in the first test is 40 mg/kg and the 50% effective dose (ED$_{50}$), administered intraduodenally, is also determined in a second test. The vehicle used is gum arabic at a concentration of 5% w/v in double-distilled water.

Two hours after ligation of the pylorus, the rats are sacrificed by prolonged anesthesia with ethyl ether and the volume of gastric juice is measured; the total acidity is determined by means of a pH meter equipped with an automatic burette. For each product and each dose tested, the percentage inhibition of gastric acid secretion is determined relative to the control group.

By way of non-limiting examples, the results obtained for some of the derivatives of the present invention are summarized in Table 13.

TABLE 13

Inhibition of gastric acid secretion in Shay rats

| Example no. | Percentage inhibition of gastric acid secretion (dose = 40 mg/kg, administered intraduodenally) | $ED_{50}$ (mg/kg, administered intraduodenally) |
|---|---|---|
| 1 | 78.7 | 22.4 |
| 5 | 96.4 | 10.8 |
| 11 | 48.8 | 42.0 |
| 14 | 61.4 | 30.6 |
| 16 | 48.0 | 42.6 |
| 18 | 41.0 | 53.5 |
| 26 | 53.0 | 38.5 |
| 28 | 51.4 | 38.5 |
| 29 | 54.2 | 37.9 |
| 34 | 63.0 | 29.9 |
| 36 | 40.0 | 65.6 |
| 62 | 52.4 | 31.0 |
| 63 | 52.0 | 49.2 |
| 68 | 53.8 | 39.7 |
| 69 | 54.3 | 39.2 |
| 73 | 77.5 | 18.5 |
| 74 | 76.4 | 17.9 |
| 90 | 51.4 | 64.0 |
| 100 | 51.8 | 37.6 |
| 102 | 71.4 | 14.1 |
| 103 | 72.3 | 15.0 |
| 115 | 51.1 | 38.9 |
| 116 | 50.3 | 39.4 |
| 127 | 56.3 | 52.4 |
| 133 | 40.0 | 58.3 |
| 134 | 70.3 | 20.7 |
| 141 | 80.9 | 16.3 |
| 142 | 79.4 | 17.5 |
| 143 | 99.3 | 20.5 |
| 144 | 93.7 | 10.0 |
| 145 | 68.7 | 19.8 |
| 146 | 67.5 | 20.3 |
| 147 | 46.5 | 44.0 |
| 148 | 45.3 | 46.0 |
| 149 | 64.0 | 32.6 |
| 150 | 53.4 | 41.6 |
| 170 | 73.2 | 21.8 |
| 173 | 57.1* | 39.2 |
| 177 | 53.7 | 38.1 |
| 180 | 43.8 | 43.7 |
| 181 | 43.4 | 62.0 |
| 182 | 42.1 | 61.2 |

Ulcer-inhibiting activity

The ulcer-inhibiting activity is demonstrated in rats by studying the inhibition of gastric lesions induced by stress due to immobilization and cold, according to the method of Senay et al. (E. C. Senay; R. J. Levine; Proc. Soc. Exp. Biol. Med., 124, 1221–1227 (1967)).

Male Wistar rats weighing 150 to 200 grams are used in this test; they are fasted in individual cages for 24 hours before the study begins, but with water "ad libitum". Groups containing a minimum of 5 animals each are used.

At the start of the study, the rats receive the products described, or alternatively the vehicle in the case of the control group, by oral administration using a stomach tube. The administered dose of the products described is 40 mg/kg. The vehicle used is gum arabic at a concentration of 5% w/v in double-distilled water.

Immediately after the treatment, the rats are introduced into confined enclosures in the form of a plastic tube with a diameter of about 5 cm and a variable length which can be adapted to the size of the rat. One hour after the treatment, the rats, in their enclosures, are placed in a refrigerator at −5° C. for 3 hours. Immediately after exposure to the cold, the rats are killed by prolonged anesthesia with ethyl ether, the stomachs are extracted and opened along the greater curvature and the lesions in the stomach mucosa are evaluated. For this evaluation, the hemorrhage points are counted and the size of the necrotic ulcers is measured.

For each product and each dose tested, the percentage inhibition of gastric lesions is determined relative to the control group.

By way of a non-limiting example, the results obtained for one of the products described are summarized in Table 14.

TABLE 14

| Product | Dose (oral administration) | No. of rats | Evaluation of the lesions ($\bar{X} \pm$ standard deviation) | Inhibition |
|---|---|---|---|---|
| Control (gum arabic) | 10 ml/kg | 10 | 6.2 ± 1.0 | — |
| Example 144 | 40 mg/kg | 10 | 0 | 100% |

Gastric cytoprotection

The gastric cytoprotective activity is demonstrated in rats by studying the inhibition of gastric lesions induced by ethanol, according to the method described by Robert et al. (A. Robert; J. E. Nezamis; C. Lancaster and A. J. Hanchar: Gastroenterology, 77: 433–443 (1979)).

Male Wistar rats weighing 150 to 200 grams are used in this test; they are fasted for 24 hours, but with water "ad libitum". Groups containing a minimum of 5 animals each are used.

At the beginning of the study, the rats receive the products described, or the vehicle in the case of the rats in the control group, by oral administration using a stomach tube. The dose administered for the products described is 40 mg/kg. The vehicle employed is gum arabic at a concentration of 5% w/v in double-distilled water.

Thirty minutes after the treatment, the rats receive 1 ml of absolute ethanol by oral administration using a stomach tube. One hour after the treatment with ethanol, the rats are sacrificed by prolonged anesthesia with ethyl ether, their stomachs are extracted and opened along the greater curvature and the lesions in the stomach mucosa are evaluated. For this evaluation, the hemorrhage points are counted and the size of the necrotic ulcers is measured.

For each product tested, the percentage inhibition of gastric lesions is determined relative to the control group.

By way of non-limiting examples, the results obtained for two of the products described are summarized in Table 15.

TABLE 15

Cytoprotection of the gastric mucosa in rats
Protection of the lesions induced by ethanol

| Product | Dose (oral administration) | No. of rats | Evaluation of the lesions ($\bar{X} \pm$ standard deviation) | Inhibition |
|---|---|---|---|---|
| Control (gum arabic) | 10 ml/kg | 16 | 27.6 ± 6.0 | — |
| Example 5 | 40 mg/kg | 5 | 4.2 ± 2.1 | 85% |
| Example 142 | 40 mg/kg | 6 | 0 | 100% |

Acute toxicity in mice

Method of Litchfield and Wilcoxon (J. T. Litchfield and E. J. Wilcoxon: J. Pharmacol. Exp. Therap., 96, 19-113 (1949)).

The product is administered orally as a suspension in gum arabic at a concentration of 5% in double-distilled water. The volume administered is 10 ml/kg. The 50% lethal dose ($LD_{50}$) is calculated by the method cited.

By way of non-limiting examples, the results obtained for some of the derivatives of the present invention are summarized in Table 16.

TABLE 16

| Product | Sex | $LD_{50}$ (mg/kg) administered orally |
|---|---|---|
| Example 6 | ♂ | 3300 |
|  | ♀ | 2600 |
| Example 8 | ♂ | 6400 |
|  | ♀ | 6400 |
| Example 16 | ♂ | 2000 |
|  | ♀ | 1500 |
| Example 18 | ♂ | 2000 |
|  | ♀ | 4000 |
| Example 21 | ♂ | >1600 |
|  | ♀ | >1600 |
| Example 31 | ♂ | >6400 |
|  | ♀ | >6400 |
| Example 34 | ♂ | >6400 |
|  | ♀ | >6400 |
| Example 38 | ♂ | >6400 |
|  | ♀ | >6400 |
| Example 71 | ♂ | 6400 |
|  | ♀ | 6400 |
| Example 92 | ♂ | 6400 |
|  | ♀ | 6400 |
| Example 99 | ♂ | >3200 |
|  | ♀ | >3200 |
| Example 127 | ♂ | >6400 |
|  | ♀ | >6400 |
| Example 128 | ♂ | >2200 |
|  | ♀ | >3200 |
| Example 133 | ♂ | >3200 |
|  | ♀ | >3200 |
| Example 134 | ♂ | >3200 |
|  | ♀ | >3200 |
| Example 179 | ♂ | >6400 |
|  | ♀ | >6400 |

In human therapy, the administered dose of the derivatives of the present invention depends of course on the severity of the complaint to be treated; it will generally be between about 30 and about 60 mg/day. The derivatives of the invention will be administered for example in the form of tablets or injectable ampoules.

By way of examples, two particular pharmaceutical forms of the derivatives forming the subject of the present invention are now indicated below.

Example of tablet formulation

| 30 mg tablets | |
|---|---|
| Example 144 | 0.030 g |
| Lactose | 0.0342 g |
| Starch | 0.030 g |
| Polyvinylpyrrolidone | 0.006 g |
| Microcrystalline cellulose | 0.018 g |
| Colloidal silicon dioxide | 0.0012 g |
| Magnesium stearate | 0.0006 g |
|  | 0.120 g |
| 60 mg tablets | |
| Example 144 | 0.060 g |
| Lactose | 0.0684 g |
| Starch | 0.060 g |
| Polyvinylpyrrolidone | 0.012 g |
| Microcrystalline cellulose | 0.036 g |
| Colloidal silicon dioxide | 0.0024 g |
| Magnesium stearate | 0.0012 g |
|  | 0.240 g |

Example of injectable ampoule formulation

| 6 mg/ml injectable ampoules | |
|---|---|
| Example 144 | 0.030 g |
| Sodium chloride q.s. | 0.050 g |
| Ascorbic acid | 0.005 g |
| Water for injection q.s. | 5 ml |

In view of the valuable pharmacological properties associated with the novel compounds of the general formula I, the present invention also covers the application of these compounds as drugs, the pharmaceutical compositions in which they are present and their use for the manufacture of drugs for the treatment of gastrointestinal diseases, in particular for the manufacture of gastric acid secretion inhibitors, ulcer inhibitors and cytoprotective agents.

What is claimed is:

1. A compound corresponding to the formula,

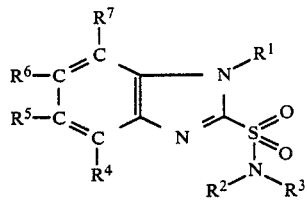

in which:

$R^1$ represents a radical selected from the group consisting of a hydrogen atom, a linear or branched alkyl radical, an alkylaryl radical, an alkylcarbonylalkyl radical, an alkylcarbonylaryl radical, an alkylcarbonylheteroaryl radical, a cycloalkyl radical and a carboxyalkyl radical, wherein the alkyl group in said alkyl and alkyl-containing radical is a $C_1$-$C_6$ alkyl group, said cycloalkyl radical contains a $C_3$-$C_{10}$ cycloalkyl group, and said aryl radical is a $C_6$ to $C_{12}$ carbocyclic aromatic group;

$R^2$ represents a radical selected from the group consisting of a hydrogen atom, a linear or branched $C_1$ to $C_5$ lower alkyl radical, a nitro radical and an $C_1$ to $C_6$ acyl radical;

$R^3$ represents a radical selected from the group consisting of a hydrogen atom, a linear or branched alkyl radical, an aryl radical, a heteroaryl radical, an alkylaryl radical, an alkylheteroaryl radical, a mono-, bi- or tri-cycloalkyl radical, an alkylamino radical, an N-alkyl-alkylamino radical, an alkylcarboxyalkyl radical, an acyl radical, an alkylthioalkyl radical, an, alkylsulfinylalkyl radical, alkylsulfonylalkyl radical, an alkylthioaryl radical, alkylsulfinylaryl radical, an alkylsulfonylaryl radical, an alkylthioheteroaryl radical, an alkylsulfinylheteroaryl radical, alkylsulfonylheteroaryl radical, an alkylthioalkylaryl radical, an alkylsulfinylalkylaryl radical, an alkylsulfonylalkylaryl radical, an alkylthioalkylheteroaryl radical, an alkylsulfinylalkylheteroaryl radical, an alkylsulfonylalkylheteroaryl radical, a halogenoalkyl radical, a cyanoalkyl radical, an N-alkylaryl-alkylamino radical, an N-alkyl-N-alkylaryl-alkylamino radical, an N,N-dialkyl-alkylamino radical, a hydroxyalkyl radical, an alkylpiperazinyl radical, an alkylpiperidinyl radical, and an alkylmorpholinyl radical, wherein the alkyl group in said alkyl and alkyl-containing radical is a $C_1$–$C_6$ alkyl group, said cycloalkyl radical is a $C_3$–$C_{10}$ cycloalkyl group, and said acyl radical is a $C_1$–$C_6$ group;

$R^4$ and $R^7$ independently represent a hydrogen atom, a halogen atom, a nitro radical, an amino radical or an acylamino radical; and $R^5$ and $R^6$ independently represent a radical selected from the group consisting of a hydrogen atom, a halogen atom, an amino radical, a nitro radical, a lower alkyl radical, a trifluoromethyl radical, an alkoxy radical, an aryloxy radical, a mercapto radical, an alkylthio radical, an alkylsulfinyl radical, an alkylsulfonyl radical, a sulfamoyl radical, an isothiocyanate radical, an alkylcarbonyl radical, an arylcarbonyl radical, an acylamino radical, a cyano radical, a carboxyl group, a carboxamido group, and a carboxyalkyl group wherein the alkyl group in said alkyl and alkyl-containing radical is a $C_1$–$C_6$ alkyl group, and said acyl radical is a $C_1$–$C_6$ group;

wherein said aryl radical is a $C_6$–$C_{12}$ carbocyclic aromatic radical; and said heteroaryl radical is a single five- to six-membered heterocyclic ring selected from the group consisting of pyridyl, isoxazolyl and morpholino radicals;

with the provisos that:

(a) when $R^1$, $R^2$, $R^4$, $R^5$, $R^6$ and $R^7$ are hydrogen, $R^3$ is not a radical selected from the group consisting of hydrogen, phenyl, m-chlorophenyl, m-tolyl, methyl, ethyl, and n-propyl;

(b) when $R^1$, $R^4$, $R^5$, $R^6$ and $R^7$ are hydrogen, $R^3$ is not phenyl when $R^2$ is methyl or carboxyethyl, and $R^3$ is not methyl when $R^2$ is methyl; and (c) when $R^1$, $R^4$, $R^6$ and $R^7$ are hydrogen and $R^5$ is methyl, $R^3$ is not phenyl when $R^2$ is hydrogen.

2. The compound according to claim 1 comprising a $R^3$-substituted-1H-benzimidazole-2-sulfonamide, wherein said $R^3$-substituent is a radical selected from the group consisting of methyl, ethyl, propyl, butyl, isopropyl, cyclohexyl, phenyl, benzyl, acetyl, benzoyl, hydroxymethyl, adamantyl, pyridyl, morpholino, and isoxazolyl.

3. A compound selected from the group consisting of:
5-Benzoyl-N-ethyl-1H-benzimidazole-2-sulfonamide,
N-[2-(4-Morpholinoethyl)-1H-benzimidazole-2-sulfonamide,
5-Chloro-N-(4-chlorophenyl)-1H-benzimidazole-2-sulfonamide,
N-Cyanomethyl-1H-benzimidazole-2-sulfonamide,
N-(5-Methyl-3-isoxazolyl)-1H-benzimidazole-2-sulfonamide,
N-[2-(2-Pyridylethyl)]-1H-benzimidazole-2-sulfonamide, and
4-Acetylamino-N-ethyl-1H-benzimidazole-2-sulfonamide.

4. Pharmaceutical compositions which contain, in addition to a pharmaceutically acceptable carrier, at least one compound according to claim 1 or one of their physiologically acceptable salts.

5. A method of treating a patient having a gastrointestinal disease which comprises administering to said patient an effective amount of a compound of the formula of claim 1 or a physiologically acceptable salt thereof.

* * * * *

UNITED STATES PATENT AND TRADEMARK OFFICE
CERTIFICATE OF CORRECTION

PATENT NO. : 4,933,338

DATED : June 12, 1990

INVENTOR(S) : Jordi F. Constansa; Juan P. Corominas and Augusto C. Piñol

It is certified that error appears in the above-identified patent and that said Letters Patent is hereby corrected as shown below:

Col. 12, line 3 (in the formula), "$R_2$" should be --$R^2$--.

Col. 14, line 43, "atome" should be --atom--.

Col. 14, line 63, "$n_3$" should be --n--.

Col. 19 at Example 13 of Table I; col. 21, at Examples 28 and 46 of Table I; and col. 23 at Example 48, the formulas appearing in the "$R^3$" column should be moved to the left so that they are in both the "$R^2$" and the "$R^3$" columns.

Col. 23, in the left column of Table I under the heading "Example No.", the numeral --54-- should be inserted to the left of the uppermost "H" in the "$R^2$" column after Example 53; the numeral --55-- should be inserted to the left of the second highest "H" in the "$R^2$" column after Example 53; the numeral --56-- should be inserted to the left of the formula "$-CH_2-CH_2-N(CH_3)-CH_2CH_2$" and the formula should be moved to the left so that it is under both columns "$R^2$" and "$R^3$"; the numeral --57-- should be inserted to the left of the next to lowest "H" in the "$R^2$" column in Table I; and the numeral --58-- should be inserted to the left of the lowest "H" in the "$R^2$" column in Table I.

Col. 25, in Table 2, Example 22, after "1.33" change "(,4H)" to --(m, 4H)--.

UNITED STATES PATENT AND TRADEMARK OFFICE
CERTIFICATE OF CORRECTION

PATENT NO. : 4,933,338

DATED : June 12, 1990

INVENTOR(S) : Jordi F. Constansa; Juan P. Corominas and Augusto C. Piñol

It is certified that error appears in the above-identified patent and that said Letters Patent is hereby corrected as shown below:

Cols. 25 and 26, the formula after Example 58 should be deleted and replaced by --TABLE 3-- followed by the formula

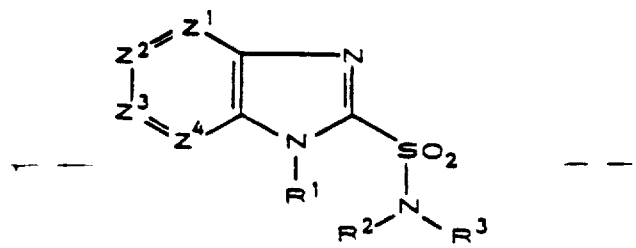

Cols. 27 and 28, top of columns, the formula should be replaced by the formula

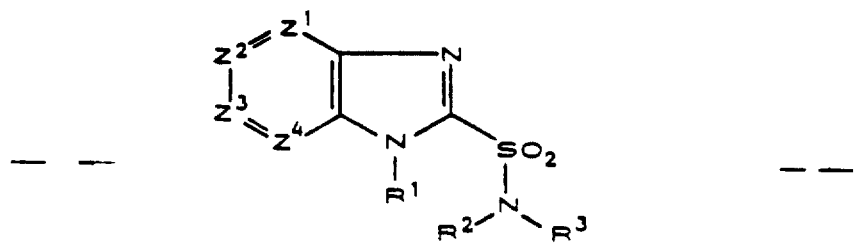

Col. 28, in Example 65 of Table 4, "5.10" should be --8.10--.

Cols. 29 and 30, above the formula near the top of the page and below the first horizontal line, insert --TABLE 5--.

Col. 35, at Example 93 of TABLE 6, "cuint" should be --quint--.

UNITED STATES PATENT AND TRADEMARK OFFICE
CERTIFICATE OF CORRECTION

PATENT NO. : 4,933,338

DATED : June 12, 1990

INVENTOR(S) : Jordi F. Constansa; Juan P. Corominas and Augusto C. Piñol

It is certified that error appears in the above-identified patent and that said Letters Patent is hereby corrected as shown below:

Col. 35, at Example 105 of TABLE 6, "(s, H)" should be --(s, 3H)--.

Col. 36, at Example 165 of TABLE 5, in the right column, "225" should be --2225--.

Col. 36, at Example 108 of TABLE 6, after "4.15", "(t, 2)" should be --(t, 2H)--.

Col. 36, at Example 116 of TABLE 6, after "4,53", "(t, 2)" should be --(t, 2H)--

Col. 36, at Example 119 of TABLE 6 (second line), "(, 7H)" should be --(m, 7H).

Col. 38, line 33, the heading "Method" should be --Method C--.

Col. 42, line 8, "hydroxide" should be --hydride--.

Col. 44, line 46, "tested" should be --fasted--.

Signed and Sealed this

Fifth Day of January, 1993

*Attest:*

DOUGLAS B. COMER

*Attesting Officer*     Acting Commissioner of Patents and Trademarks